US012332254B2

(12) United States Patent
Abbott et al.

(10) Patent No.: US 12,332,254 B2
(45) Date of Patent: Jun. 17, 2025

(54) SYSTEMS, COMPOSITIONS, AND METHODS FOR EVALUATING BIOMECHANICAL PROPERTIES OF CELLS

(71) Applicant: CORNELL UNIVERSITY, Ithaca, NY (US)

(72) Inventors: Nicholas Abbott, Ithaca, NY (US); Karthik Nayani, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 865 days.

(21) Appl. No.: 17/605,792

(22) PCT Filed: Apr. 24, 2020

(86) PCT No.: PCT/US2020/029738
§ 371 (c)(1),
(2) Date: Oct. 22, 2021

(87) PCT Pub. No.: WO2020/219825
PCT Pub. Date: Oct. 29, 2020

(65) Prior Publication Data
US 2022/0206020 A1 Jun. 30, 2022

Related U.S. Application Data

(60) Provisional application No. 62/837,959, filed on Apr. 24, 2019.

(51) Int. Cl.
*G01N 33/80* (2006.01)
*C09K 19/06* (2006.01)
(Continued)

(52) U.S. Cl.
CPC .......... *G01N 33/80* (2013.01); *C09K 19/061* (2013.01); *C09K 19/3402* (2013.01);
(Continued)

(58) Field of Classification Search
CPC ........ G01N 33/80; G01N 1/36; C09K 19/061; C09K 19/3402; C09K 19/3819;
(Continued)

(56) References Cited

U.S. PATENT DOCUMENTS 3,955,890 A 5/1976 Bessis
4,428,669 A 1/1984 Bessis
(Continued)

FOREIGN PATENT DOCUMENTS

WO 2017/150971 A1 9/2017

OTHER PUBLICATIONS

Abay A. et al., "Glutaraldehyde-A Subtle Tool in the Investigation of Healthy and Pathologic Red Blood Cells", Frontiers in Physiology 10(514):1-14 (May 2019).
(Continued)

*Primary Examiner* — Brian J. Sines
(74) *Attorney, Agent, or Firm* — Scully, Scott, Murphy & Presser, P.C.

(57) ABSTRACT

The response of biological cells to applied stress is central to the functioning of living systems. The present disclosure is directed to systems, compositions and methods for rapidly reporting biomechanical properties of cells or cellular organelles at a single cell or population level.

25 Claims, 12 Drawing Sheets

(51) Int. Cl.
   *C09K 19/34* (2006.01)
   *C09K 19/38* (2006.01)
   *G01N 1/36* (2006.01)
   *G06T 7/00* (2017.01)

(52) U.S. Cl.
   CPC ........... *C09K 19/3819* (2013.01); *G01N 1/36* (2013.01); *G06T 7/0012* (2013.01); *C09K 2019/3425* (2013.01); *G06T 2207/10056* (2013.01); *G06T 2207/30024* (2013.01)

(58) Field of Classification Search
   CPC .......... C09K 2019/3425; G06T 7/0012; G06T 2207/10056; G06T 2207/30024
   See application file for complete search history.

(56) References Cited

U.S. PATENT DOCUMENTS

| | | | |
|---|---|---|---|
| 4,521,729 | A | 6/1985 | Kisewetter et al. |
| 5,376,878 | A | 12/1994 | Fisher et al. |
| 5,531,925 | A | 7/1996 | Landh et al. |
| 5,798,827 | A | 8/1998 | Frank et al. |
| 7,018,838 | B2 | 3/2006 | Murphy et al. |
| 7,303,694 | B2 | 12/2007 | Murphy et al. |
| 7,460,240 | B2 | 12/2008 | Akcakir |
| 8,021,570 | B2 | 9/2011 | Gellman et al. |
| 8,026,102 | B2 | 9/2011 | Tarasev et al. |
| 8,097,457 | B2 | 1/2012 | Abbott et al. |
| 8,133,680 | B2 | 3/2012 | Abbott et al. |
| 8,278,040 | B2 | 10/2012 | Abbott et al. |
| 9,625,721 | B1 | 4/2017 | Verduzco et al. |
| 9,796,962 | B2 | 10/2017 | Osafune et al. |
| 2005/0064395 | A1 | 3/2005 | Israel et al. |
| 2006/0063882 | A1 | 3/2006 | Velev et al. |
| 2009/0269323 | A1 | 10/2009 | Luk et al. |
| 2010/0021344 | A1 | 1/2010 | Gellman et al. |
| 2011/0183439 | A1 | 7/2011 | Bazan et al. |
| 2012/0273993 | A1 | 11/2012 | Shoseyov et al. |
| 2013/0183711 | A1 | 7/2013 | Sjong |
| 2014/0017718 | A1 | 1/2014 | Tarasev et al. |
| 2016/0222137 | A1 | 8/2016 | Mousa |
| 2017/0000903 | A1 | 1/2017 | Olkowski et al. |
| 2017/0299571 | A1 | 10/2017 | Slepian et al. |
| 2019/0111185 | A1 | 4/2019 | Hegmann et al. |

OTHER PUBLICATIONS

Bao G. et al., "Cell and Molecular Mechanics of Biological Materials", Nature Materials 2:715-725 (Nov. 2003).
Barthès-Biesel D. et al., "Effect of Constitutive Laws for Two-Dimensional Membranes on Flow-Induced Capsule Deformation", J. Fluid Mech. 460:211-222 (2002).
Canham P.B. et al., "The Area and Volume of Single Human Erythrocytes During Gradual Osmotic Swelling to Hemolysis", Canadian Journal of Physiology and Pharmacology 48(6):369-376 (1970).
Chen C.S. et al., "Geometric Control of Cell Life and Death", Science 276(5317):1425-1428 (May 30, 1997).
Dao M. et al., "Mechanics of the Human Red Blood Cell Deformed by Optical Tweezers", Journal of Mechanics and Physics of Solids 51(11):2259-2280 (2003).
Davidson Z.S. et al., "Chiral Structures and Defects of Lyotropic Chromonic Liquid Crystals Induced by Saddle-Splay Elasticity", Physical Review E 91(5):050501 (2015).
Deschamps J. et al., "Dynamics of a Vesicle in General Flow", PNAS 106(28):11444-11447 (Jul. 14, 2009).
Deserno M., "Fluid Lipid Membranes: From Differential Geometry to Curvature Stresses", Chemistry and Physics of Lipids 185:11-45 (2015).
Engelhardt H. et al., "On the Measurement of Shear Elastic Moduli and Viscosities of Erythrocyte Plasma Membranes by Transient Deformation in High Frequency Electric Fields", Biophys J. 54(3):495-508 (Sep. 1988).
Engström K.G. et al., "Effects of Pressure on Red Blood Cell Geometry During Micropipette Aspiration", Cytometry 23(1):22-27 (1996).
Fedosov D.A. et al., "A Multiscale Red Blood Cell Model With Accurate Mechanics, Rheology, and Dynamics", Biophysical Journal 98(10):2215-2225 (May 2010).
Fletcher D.A. et al., "Cell Mechanics and the Cytoskeleton", Nature 463(7280):485-492 (Jan. 28, 2010).
Hasler C.R. et al., "Echinocytosis Induced by Haemodialysis", Nephrology Dialysis Transplantation 13(12):3132-3137 (1998).
Ki-Kim Y. et al., "Self-Reporting and Self-Regulating Liquid Crystals", Nature 557:539-544 (May 24, 2018).
Koslov M.M. et al., "A Theory of Osmotic Lysis of Lipid Vesicles", J. Theor. Biol. 109(1):17-39 (1984).
Mushenheim P.C. et al., "Straining Soft Colloids in Aqueous Nematic Liquid Crystals", PNAS 113(20):5564-5569 (May 17, 2016).
Nayani K. et al., "Spontaneous Emergence of Chirality in Achiral Lyotropic Chromonic Liquid Crystals Confined to Cylinders", Nature Communications 6:8067 (2015).
Ohno M. et al., "Dynamic Behavior of Giant Liposomes at Desired Osmotic Pressures", Langmuir 25(19):11680-11685 (2009).
Oliver P.M. et al., "Localization of Anionic Phospholipids in *Escherichia Coli* Cells", Journal of Bacteriology 196(19):3386-3398 (Oct. 2014).
Peng Z. et al., "Lipid Bilayer and Cytoskeletal Interactions in a Red Blood Cell", PNAS 110(33):13356-13361 (Aug. 13, 2013).
Pivkin I.V. et al., "Accurate Coarse-Grained Modeling of Red Blood Cells", Physical Review Letters 101(11):118105 (2008).
Puig-De-Morales-Marinkovic M. et al., "Viscoelasticity of the Human Red Blood Cell", Am J Physiol Cell Physiol 293:C597-C605 (2007).
Rappaz B. et al., "Comparative Study of Human Erythrocytes by Digital Holographic Microscopy, Confocal Microscopy, and Impedance Volume Analyzer", Cytometry Part A 73A(10):895-903 (2008).
Renner L.D. et al., "Cardiolipin Microdomains Localize to Negatively Curved Regions of *Escherichia Coli* Membranes", PNAS 108(15):6264-6269 (Apr. 12, 2011).
Rudenko S.V. et al., "Determination of Time-Dependent Shape Changes in Red Blood Cells", Biochemistry (Moscow) 63(12):1385-1394 (1998).
Sheetz M.P. et al., "Biological Membranes as Bilayer Couples", The Journal of Cell Biology 70(1):193-203 (1976).
Skalak R. et al., "Strain Energy Function of Red Blood Cell Membranes", Biophysical Journal 13(3):245-264 (1973).
Svoboda K. et al., "Conformation and Elasticity of the Isolated Red Blood Cell Membrane Skeleton", Biophys. 63(3):784-793 (Sep. 1992).
Tortora L. et al., "Chiral Symmetry Breaking by Spatial Confinement in Tactoidal Droplets of Lyotropic Chromonic Liquid Crystals", PNAS 108(13):5163-5168 (Mar. 29, 2011).
Wang N. et al., "Mechanotransduction Across the Cell Surface and Through the Cytoskeleton", Science 260(5111):1124-1127 (May 21, 1993).
Zhang L. et al., "Free Energy Calculations for the Peripheral Binding of Proteins/Peptides to an Anionic Membrane.1. Implicit Membrane Models", Journal of Chemical Theory and Computation 10(7):2845-2859 (2014).
Zhou S. et al., "Elasticity, Viscosity, and Orientational Fluctuations of a Lyotropic Chromonic Nematic Liquid Crystal Disodium Cromoglycate", Soft Matter 10(34):6571-6581 (2014).
International Search Report dated Aug. 25, 2020 received in International Application No. PCT/US20/29738.

SYSTEMS, COMPOSITIONS, AND METHODS FOR EVALUATING BIOMECHANICAL PROPERTIES OF CELLS

CROSS REFERENCE TO RELATED APPLICATION

This application claims the benefit of priority from U.S. Provisional Application No. 62/837,959, filed Apr. 24, 2019, the entire contents of which are incorporated herein by reference.

STATEMENT REGARDING FEDERALLY SPONSORED RESEARCH OR DEVELOPMENT

This invention was made with government support under Grant No. CBET-1852379 awarded by National Science Foundation and Grant Nos. W911NF-16-1-0154 and W911NF-19-1-0071, awarded by the Army Research Office. The government has certain rights in the invention.

BACKGROUND

Dynamic management of mechanical strain is one of the central principles by which living systems regulate their organization and functional properties (Fletcher D A & Mullins R D (2010), *Nature*, 463:485; Moeendarbary E & Harris A R (2014), *Wiley interdisciplinary reviews. Systems biology and medicine* 6(5):371-388). Curvature strains within bacterial cell membranes are known to locally concentrate specific lipids and proteins to regions of high membrane curvature to facilitate cell division (Oliver P M, et al. (2014), *J. Bacteriol.* 196(19):3386-3398; Renner L D & Weibel D B (2011), *Proc. Natl. Acad. Sci. U.S.A* 108(15): 6264-6269; Zhang L L, Yethiraj A, & Cui Q (2014) *J. Chem. Theory Comput.* 10(7):2845-2859; Laloux G & Jacobs-Wagner C (2014) *Journal of Cell Science* 127(1):11; Mohammadi H & Sahai E (2018) *Nature Cell Biology* 20(7):766-774; Chen C S et al. (1997), *Science* 276(5317): 1425), and mammalian cells respond to their mechanical environment by changing their internal organization, gene expression and phenotype (Renner L D & Weibel D B (2011), *Proc. Natl. Acad. Sci. U.S.A* 108(15):6264-6269; Mohammadi H & Sahai E (2018) *Nature Cell Biology* 20(7):766-774). For example, red blood cells (RBCs), when strained by shear flows in narrow capillaries of the body, dynamically regulate their cytoskeletons to change their mechanical properties (Wang N et al., (1993), *Science* 260(5111):1124-1127). Disruption of the dynamic mechanical response can result in hematologic diseases (Maciaszek J L & Lykotrafitis G (2011), *J. Biomech.* 44(4):657-661; Bao G & Suresh S (2003), *Nat. Mater.* 2(11):715-725) such as Sickle cell disease; diseased cells are stiffer and exhibit shapes (e.g., crescent-like shapes) that differ from healthy cells leading to changes in the rheological properties of blood such as cell distribution and the blocking of capillaries by stiff cells (Maciaszek J L & Lykotrafitis G (2011), *J. Biomech.* 44(4):657-661; Lam W A et al., (2008), *Br. J. Haematol.* 142(3):497-501; Mushenheim P C et al., (2016), *Proc. Natl. Acad. Sci. U.S.A* 113(20):5564-5569). Facile methods to characterize the mechanical properties of red blood cells, particularly at the individual cell level, are needed to characterize cell-to-cell variation in properties of populations of RBCs (Fletcher D A & Mullins R D (2010), *Nature*, 463:485; Moeendarbary E & Harris A R (2014), *Wiley interdisciplinary reviews. Systems biology and medicine* 6(5):371-388).

SUMMARY OF THE DISCLOSURE

An aspect of the disclosure is directed to a system, comprising a liquid crystal material, and a device for holding a cell or an organelle of a cell, and the liquid crystal material, wherein the device is designed for use in optical imaging the cell or the organelle in the presence of the liquid crystal material at an isotonic concentration. In some embodiments, the device comprises a surface that is optically transparent. In some embodiments, the device comprises a cuvette or a slide. In some embodiments, the device has at least one port.

In some embodiments, the system further comprises an imaging apparatus. In some embodiments, the imaging apparatus is selected from an optical microscope, a confocal microscope or a camera.

Another aspect of the disclosure is directed to a composition comprising a liquid crystal material at an isotonic concentration and a cell or an organelle of a cell.

Another aspect of the disclosure is directed to a method of evaluating a cell or an organelle of a cell, comprising detecting the state of the cell or the organelle in a liquid crystal material; comparing the state of the cell to a state of a control cell or a state of a control organelle, thereby determining a biomechanical property of the cell or the organelle.

In some embodiments, the state of the cell or the organelle of the cell comprises the shape of the cell or the shape of the organelle. In some embodiments, a difference between the state of the cell or the organelle of the cell and the state of the control cell or the control organelle indicates the health status of the cell.

Another aspect of the disclosure is directed to a method of evaluating a cell or an organelle of a cell, comprising detecting a first state of the cell or the organelle in an aqueous buffer; detecting a second state of the cell or the organelle in a liquid crystal material; comparing the first state of the cell or the organelle to the second state of the cell or the organelle, thereby determining a biomechanical property of the cell.

In some embodiments, the first state and the second state of the cell or the organelle comprise the shape of the cell or the organelle. In some embodiments, a difference between the first state of the cell or the organelle and the second state of the cell or the organelle indicates the health status of the cell or the organelle.

Another aspect of the disclosure is directed to a method of evaluating a cell or an organelle of a cell, comprising placing the cell or the organelle in a liquid crystal material at a first state, and detecting a first state of the cell or the organelle; effecting a change in the liquid crystal material from the first state to a second state, and detecting a second state of the cell or the organelle after the change; wherein the first state of the liquid crystal material is less ordered than the second state of the liquid crystal material, or the first state of the liquid crystal material is more ordered than the second state of the liquid crystal material; and comparing the first state of the cell or the organelle to the second state of cell or the organelle, thereby determining a biomechanical property of the cell or the organelle.

In some embodiments, the first and the second state of the cell or the organelle comprise the shape of the cell or the organelle. In some embodiments, a difference between the first state of the cell or the organelle and the second state of the cell or the organelle indicates the health status of the cell or the organelle. In some embodiments, the change in the liquid crystal material is effected by a change in temperature or a change in concentration of the liquid crystal material.

Another aspect of the disclosure is directed to a method of evaluating cells or organelles of cells, comprising placing the cells or the organelles in a liquid medium, wherein a part of the liquid medium is in a liquid crystal state, and another part of the liquid medium is in a isotropic state, and wherein a first group of cells or organelles are in the part of the liquid medium that is in the liquid crystal state, and a second group of cells or organelles are in the part of the liquid medium that is in the isotropic state; detecting a state of the first group of cells or organelles and a state of the second group of cells or organelles; comparing the state of the first group of cells or organelles to the state of the second group of cells or organelles, thereby determining a biomechanical property of the cells or the organelles.

In some embodiments, the state of the first group of cells or the organelles and the state of the second group of cells or the organelles comprise the shape of the cells or the organelles. In some embodiments, a difference between the state of the first group of cells or organelles and the state of the second group of cells or organelles indicates the health status of the cells or the organelles.

In some embodiments, the liquid crystal material is at an isotonic concentration. In some embodiments, the liquid crystal material is a lyotropic liquid crystal. In some embodiments, the lyotropic liquid crystal is a non-amphiphilic liquid crystal. In some embodiments, the non-amphiphilic liquid crystal is a chromonic lyotropic liquid crystal. In some embodiments, the chromonic lyotropic liquid crystal is a disodium chromoglycate (DSCG)-based liquid crystal. In some embodiments, the non-amphiphilic liquid crystal is colloidal liquid crystal. In some embodiments, the colloidal liquid crystal comprises cellulose. In some embodiments, the non-amphiphilic liquid crystal is liquid crystal comprised of polymers or oligomers. In some embodiments, the polymers or the oligomers are selected from alpha peptides or beta peptides.

In some embodiments, the cell is a eukaryotic cell. In some embodiments, the cell is a mammalian cell. In some embodiments, the cell is a plant cell. In some embodiments, the cell is a human cell. In some embodiments, the cell is a red blood cell. In some embodiments, the red blood cell is from a human suspected to be suffering from malaria or sickle cell anemia. In some embodiments, the organelle is a chloroplast.

DETAILED DESCRIPTION

Figures 1A, 1B, 1C, 1D:
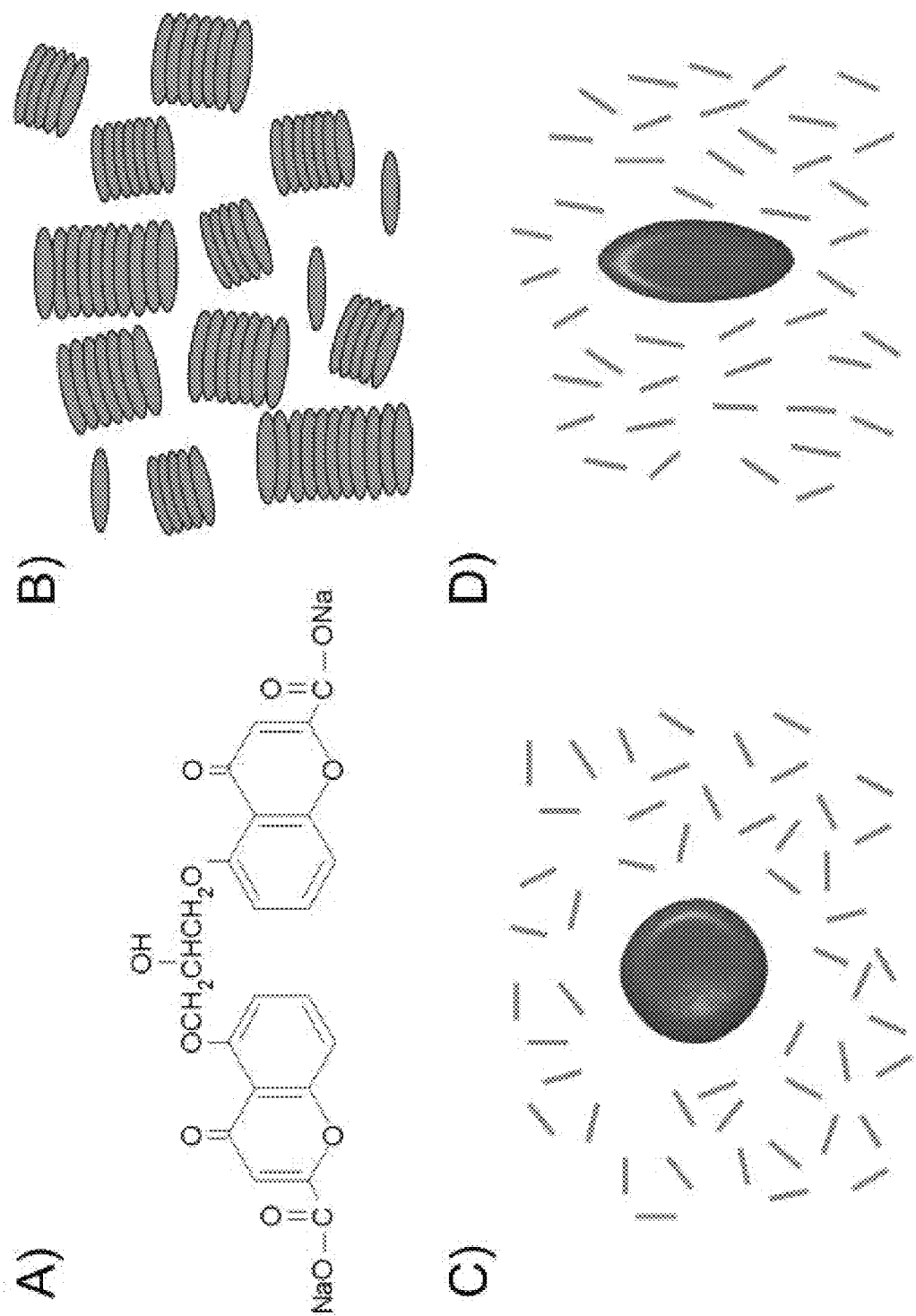
FIGS. 1A-1D. (A) Molecular structure of DSCG. (B) Schematic illustration of the self-assembly of DSCG molecules into columnar aggregates that exhibit long-range orientational order. (C and D) Schematic illustrations of RBCs suspended in aqueous solutions of DSCG in (C) isotropic and (D) nematic phases.

The inventors of this disclosure have found systems, compositions and methods for determining biomechanical properties of a cell or an organelle of a cell using liquid crystal materials. The instant disclosure systems, compositions and methods that can characterize cells or organelles individually (i.e., at single cell or single organelle level) or as a population.

In some aspects, the disclosure is directed at characterizing global shape changes of cells/organelles in response to an applied elastic stress produced by liquid crystal materials.

The methods of the disclosure do not require complex instrumentation and are versatile (can be adopted for a range of biological specimens). The methods of the instant disclosure are also rapid and can determine biomechanical properties of a cell or an organelle in minutes.

Cells or Organelles of a Cell

In one aspect, the systems, compositions and methods of the instant disclosure involve cells. In some embodiments, the cell is a eukaryotic cell.

In some embodiments, the cell is a mammalian cell or a plant cell. In some embodiments, the mammalian cell is a human cell. In some embodiments, the human cell is a red blood cell. In some embodiments, the red blood cell is from a human suspected to suffer from malaria or sickle cell anemia.

In another aspect, the systems, compositions and methods of the instant disclosure involve a biological structure with a size between about 1 micrometer and 100 micrometers. In some embodiments, the biological structure comprises or is an organelle of a cell. In some embodiments, the organelle is a chloroplast.

Liquid Crystal Materials

In one aspect, the systems, compositions and methods of the instant disclosure utilize liquid crystal materials. Liquid crystals of the instant disclosure are non-toxic to living cells.

The phrase "liquid crystal material" refers to a substance which flows like a liquid but has some degree of ordering in the arrangement of its molecules. A "mesogen," as used herein, refers to a compound that displays liquid crystal properties. Liquid crystals can be described as disordered solids or ordered liquids because they arise from a unique state of matter that exhibits both solid- and liquid-like properties.

In some embodiments, the liquid crystal material is a lyotropic liquid crystal. As used herein, a "lyotropic liquid crystal" refers to a liquid crystal formed by dissolving a mesogen in a suitable solvent, under appropriate conditions of concentration, temperature and pressure. In some embodiments, lyotropic liquid crystals are liquids that exhibit long-range molecular ordering, can host and impart anisometric elastic stresses to strain any cell or organelle within. In some embodiments, the elasticity of the liquid crystals generates mechanical stresses that drive reversible changes in cell shape.

In some embodiments, the liquid crystal material is a non-amphiphilic liquid crystal. As used herein, the term "non-amphiphilic" refers to molecules that are not amphiphilic (an amphiphilic compound is a chemical compound possessing both hydrophilic (water-loving, polar) and lipophilic (fat-loving) properties), i.e., unlike detergents. Non-amphiphilic molecules have a lower tendency to disrupt cell membranes than amphiphilic molecules.

In some embodiments, the liquid crystal material is a lyotropic chromonic liquid crystal. As used herein, a "chromonic liquid crystal" refers to a liquid crystal that has a structure of linear aggregates made up of relatively flat molecules. In some embodiments, the chromonic lyotropic liquid crystal is a disodium chromoglycate (DSCG)-based liquid crystal. In some embodiments, the chromonic lyotropic liquid crystal is a Sunset Yellow (Disodium 6-hydroxy-5-[(4-sulfophenyl)azo]-2-naphthalenesulfonate)-based liquid crystal. In some embodiments, the chromonic lyotropic liquid crystal molecules are stacked into anisometric columnar assemblies, via $\pi$-$\pi$ interactions of their polyaromatic cores, which in turn exhibit long-range orientation-order and give rise to mesophases with anisotropic elastic properties.

In some embodiments, a non-amphiphilic liquid crystal is colloidal liquid crystal. In some embodiments, a colloidal liquid crystal comprises cellulose. The cellulose can be in nanoparticulate form, often referred to as nanocellulose.

In some embodiments, a non-amphiphilic liquid crystal is liquid crystal comprised of polymers or oligomers. In some embodiments, the polymers or the oligomers are selected from alpha peptides or beta peptides.

In some embodiments, the liquid crystal materials of the instant disclosure are selected from the liquid crystal materials disclosed in U.S. Pat. Nos. 8,021,570; 8,097,457; 8,278,040; 8,133,680; 8,021,570; and US Publication No: US2005/0064395; all of which are incorporated herein in their entirety.

Systems

In one aspect, the instant disclosure is directed to a system comprising a liquid crystal material, and a device for holding (i) a cell or an organelle of a cell and (ii) the liquid crystal material, wherein the device is designed for use in optical imaging the cell or the organelle in the presence of the liquid crystal material at an isotonic concentration.

In some embodiments, the device designed for use in optical imaging comprises a surface that is optically transparent. In some embodiments, the device comprises a cuvette or a slide. In some embodiments, the device comprises at least one port. In some embodiments, the at least one port is used to input cells/organelles and/or liquid crystal material into the device.

In some embodiments, the system further comprises an imaging apparatus. In some embodiments, the imaging apparatus is selected from an optical microscope, a confocal microscope or a camera. In a specific embodiment, the camera is a cell phone camera.

Compositions

In one aspect, the instant disclosure is directed to a composition comprising (i) a liquid crystal material at an isotonic concentration and (ii) a cell or an organelle of a cell.

Methods of Evaluating a Cell

In one aspect, the instant disclosure is directed to a method of evaluating a cell or an organelle of a cell, comprising detecting the state of the cell or the organelle in a liquid crystal material; comparing the state of the cell to a state of a control cell or a state of a control organelle, thereby determining a biomechanical property of the cell or the organelle.

A biomechanical property of a cell or a cell organelle includes, for example, deformability, flexibility, shear modulus, bending modulus and extensional modulus, viscoelasticity and relaxation time constant. The phrase "relaxation time constant" refers to the time that a deformed cell takes to recover its original shape. In a specific embodiment where the cell is a red blood cell, "relaxation time constant" refers to the time that a deformed red blood cell takes to recover its original biconcave shape. For example, the shape can reflect deformability/flexibility of a cell, or the shear modulus of a cell, which in turn is indicative of the health status. So the shape is the state being evaluated, and the deformability/flexibility or shear modulus is the biomechanical property.

In some embodiments, a cell or a cell organelle is put under elastic stress, and subsequently the elastic stress on the cell or the organelle is removed. In some embodiments, high elastic stress is imparted on the cell or cell organelle by a liquid crystal material. Following the removal of the stress, the time it takes for the cell or the organelle (relaxation time constant) is measured, which indicates the health status.

In some embodiments, the liquid crystal material is at an isotonic concentration.

In some embodiments, the control cell/organelle is a normal healthy cell/organelle of the same type as the cell/organelle. In some embodiments, a difference between the state of the cell and the state of the control cell indicates the health status of the cell. In some embodiments, the state of the control cell is predetermined in the same liquid crystal material under the same conditions.

In some embodiments, the state of the cell or the organelle of the cell comprises the shape of the cell or the shape of the organelle.

In another aspect, the instant disclosure is directed to a method of evaluating a cell/organelle, comprising detecting a first state of the cell/organelle in an aqueous solution; detecting a second state of the cell/organelle in a liquid crystal material; comparing the first state of the cell to the second state of cell, thereby determining a biomechanical property of the cell. In some embodiments, the cell is in an isotonic aqueous solution. In some embodiments, the aqueous solution exerts less elastic stress on the cell/organelle than the liquid crystal material.

In some embodiments, a cell/organelle is first placed in an aqueous solution, and the cell/organelle is then placed in a liquid crystal material. In some embodiments, the shape of the cell/organelle is deformed when placed in the liquid crystal material as compared to its shape in the aqueous solution. In some embodiments, a deformation in shape indicates biomechanical properties of the cell/organelle.

In some embodiments, a cell/organelle is first placed in a liquid crystal material, and the cell/organelle is then placed in an aqueous solution. In some embodiments, the shape of the cell/organelle is more deformed in the liquid crystal material as compared to its shape in the aqueous solution. Upon placement into the aqueous solution from the liquid crystal material, the elastic stress on the cell/organelle is lost, and the cell/organelle assumes its original/default shape (i.e., the shape of the cell/organelle with no elastic stress applied). In some embodiments, the time to return to original shape is indicative of the biomechanical properties of the cell.

In some embodiments, the aqueous solution and the liquid crystal material are at an isotonic concentration. In some embodiments, the aqueous solution is an aqueous buffer. In some embodiments, the aqueous buffer comprises a saline solution, a phosphate-buffered saline (PBS) solution, 4-(2-hydroxyethyl)-1-piperazineethanesulfonic acid) (HEPES); N-cyclohexyl-3-aminopropanesulfonic acid (CAPS); (3-(N-morpholino)propanesulfonic acid) (MOPS); or 2-(N-morpholino)ethanesulfonic acid (MES).

In some embodiments, the first state and the second state of the cell/organelle comprise the shape of the cell/organelle.

In some embodiments, a difference between the first state of the cell/organelle and the state of the cell indicates the health status of the cell/organelle. In some embodiments, a healthy cell is deformed under elastic stress and assumes its original shape rapidly once the elastic stress is removed.

In another aspect, the instant disclosure is directed to a method of evaluating a cell/organelle, comprising placing the cell/organelle in a liquid crystal material at a first state, and detecting a first state of the cell/organelle; effecting a change in the liquid crystal material from the first state to a second state, and detecting a second state of the cell/organelle after the change; wherein the first state of the liquid crystal material is less ordered than the second state of the liquid crystal material, or the first state of the liquid crystal material is more ordered than the second state of the liquid crystal material; and comparing the first state of the cell/organelle to the second state of cell, thereby determining a biomechanical property of the cell/organelle.

For instance, in some embodiments, a cell/organelle is placed in a liquid crystal material and the packing order of the liquid crystal material is increased. In some embodiments, the packing order is increased by decreasing the temperature of the liquid crystal. In other embodiments, the packing order is increased by increasing the concentration of the liquid crystal material. In some embodiments, the molecules of the liquid crystal material stack into anisometric columnar assemblies, via $\pi$-$\pi$ interactions of their polyaromatic cores, thereby increasing the elastic stress it can impart on any cell/organelle within.

In some embodiments, a liquid crystal state exerts more force or torque on a cell or an organelle within the liquid crystal when the liquid crystal is in a more ordered state (i.e., the liquid crystal is in a higher packing order).

In some embodiments, the first state and the second state of the cell/organelle comprise the shape of the cell/organelle.

In some embodiments, a difference between the first state of the cell/organelle and the second state of the cell indicates the health status of the cell/organelle. In some embodiments, healthy cells can deform when elastic stress is increased whereas unhealthy cells cannot deform, or cannot deform as much as healthy cells.

In some embodiments, the change in the liquid crystal material is achieved by a change in temperature or a change in concentration of the liquid crystal material. In some embodiments, the liquid crystal has a more ordered state when the concentration of the liquid crystal increases. In some embodiments, the liquid crystal has a more ordered state when the concentration of the liquid crystal material is increased. In some embodiments, the liquid crystal has a more ordered state when the temperature of the liquid crystal material is decreased.

In another aspect, the instant disclosure is directed to a method of evaluating cells/organelles, comprising placing the cells/organelles in a liquid medium wherein a part of the liquid medium is in a liquid crystal (anisotropic) state, and another part of the liquid medium is in an isotropic state, and wherein a first group of the cells/organelles are in the part of the liquid medium that is in the liquid crystal state, and a second group of the cells/organelles are in the part of the liquid medium that is in the isotropic state; detecting a state of the first group of cells and a state of the second group of cells; comparing the state of the first group of cells to the state of the second group of cells, thereby determining a biomechanical property of the cells.

In some embodiments, the liquid medium comprises a liquid crystal material. In some embodiments, the liquid crystal material is a lyotropic liquid crystal.

In some embodiments, the state of the first group of cells/organelles and the state of the second group of cells/organelles comprise the shape of the cells/organelles.

In some embodiments, a difference between the state of the first group of cells/organelles and the state of the second group of cells/organelles indicates the health status of the cells/organelles.

In some embodiments, healthy cells deform under elastic stress, and unhealthy cells preserve their shape or deform less than healthy cells. In a specific embodiment, the cells are red blood cells from a subject suspected to have sickle cell anemia and the subject is determined to be healthy if the cells deform under increased elastic stress, and the subject is determined to have sickle cell anemia if the cells are stiff and do not deform under increased elastic stress or do not deform as much as the cells from the healthy subject. In a specific embodiment, the cells are red blood cells from a subject suspected to have malaria and the subject is determined to be healthy if the cells deform under increased elastic stress, and the subject is determined to have malaria if the cells are stiff and do not deform under increased elastic stress or deform less than the healthy cells.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Materials. Healthy human RBCs were purchased from Innovative Research Inc and re-dispersed in isotonic solution of NaCl (154 mM) following ultracentrifugation. For dispersion of RBCs in 17.3 wt % DSCG, 1 vol % of the RBCs dispersed in isotonic NaCl solutions were measured out and pipetted into the DSCG solutions. The resulting mixture was gently mixed with a vortexer. Polyamide (PI) coated glass slides were made using procedures described previously to create sandwich cells of 100 μm spacing to align the LC. The RBCs dispersed in DSCG were filled into the PI coated glass sandwich cells with the help of capillary action. The membrane staining dye 1, 1' dioctadecyl-3, 3, 3', 3' tetramethylindodicarbocyanine, 4-chlorobenezenesulfonate salt (DiD') was purchased from Avanti Polar Lipids, Inc. (Alabaster, AL) and used to stain RBCs for confocal scanning microscopy experiments. Disodium cromoglycate was purchased from Sigma-Aldrich (Milwaukee, WI). Fisher's Finest Premium grade glass slides and cover glass were purchased from Fisher Scientific (Pittsburgh, PA). Deionization of a distilled water source was performed with a Milli-Q system (Millipore, Bedford, MA) to give water with a resistivity of 18.2 MΩ cm.

Microscopy. RBCs dispersed in 17.3 wt % DSCG and isotonic NaCl solutions were imaged using an Olympus BX60 upright microscope equipped with a 60× and 50× objectives, crossed polarizers, and a 100 W mercury lamp. Images were captured using a digital camera (Olympus C-2040 Zoom) mounted on the microscope and set to a f-stop of 2.8 and a shutter speed of 1/15 s.

Confocal Fluorescence Microscopy. The 3-D rendering of the strained RBC shapes was obtained using a Carl Zeiss LSM 700 laser confocal scanning microscope. The RBCs were dispersed in isotonic NaCl solutions and stained with a membrane staining dye (DiD) at concentrations of 15 μM for a period of 3 hrs at a temperature of 30° C. Stained cells were then ultra-centrifuged and washed in isotonic NaCl solutions twice before dispersing them in DSCG solutions. 63× water immersion objectives were used to obtain the z-stack images of strained RBCs. Zen Blue software was in imaging the strained RBCs and 3-D viewer plugin of Fiji software was employed for constructing the 3-D render of the RBCs.

Dispersing RBCs in Lyotropic LCs. Lyotropic LCs containing DSCG were prepared by mixing 17.3 wt % of DSCG with 82.7 wt % water. The mixture was placed on a shaker for at least 4 hours to ensure homogeneity. 0.5 vol % (0.5 μL) of RBCs dispersed in isotonic aqueous NaCl solutions were then added to the (100 μL) DSCG solution and gently stirred to disperse the RBCs in the DSCG solution. The pH of the 17.3 wt % DSCG solution as prepared was measured to be 9.2. The inventors used 1M HCl solutions to lower the pH to 7.4. The experimental results presented in this disclosure were found to be independent of pH for values between 9.2 and 7.4.

Vapor pressure Osmometry. VAPRO 5520 vapor pressure osmometers (Logan, UT) were used to measure the osmotic pressures of DSCG at different concentrations and compared with a reference measurement of the osmotic pressure of 154 mM NaCl solution measured using the same instrument. The vapor pressure osmometer measures the activity of water in a solution at a given temperature. For each solute, averages of the data obtained for four separate runs were reported in FIG. 2.

Figures 7A, 7B:
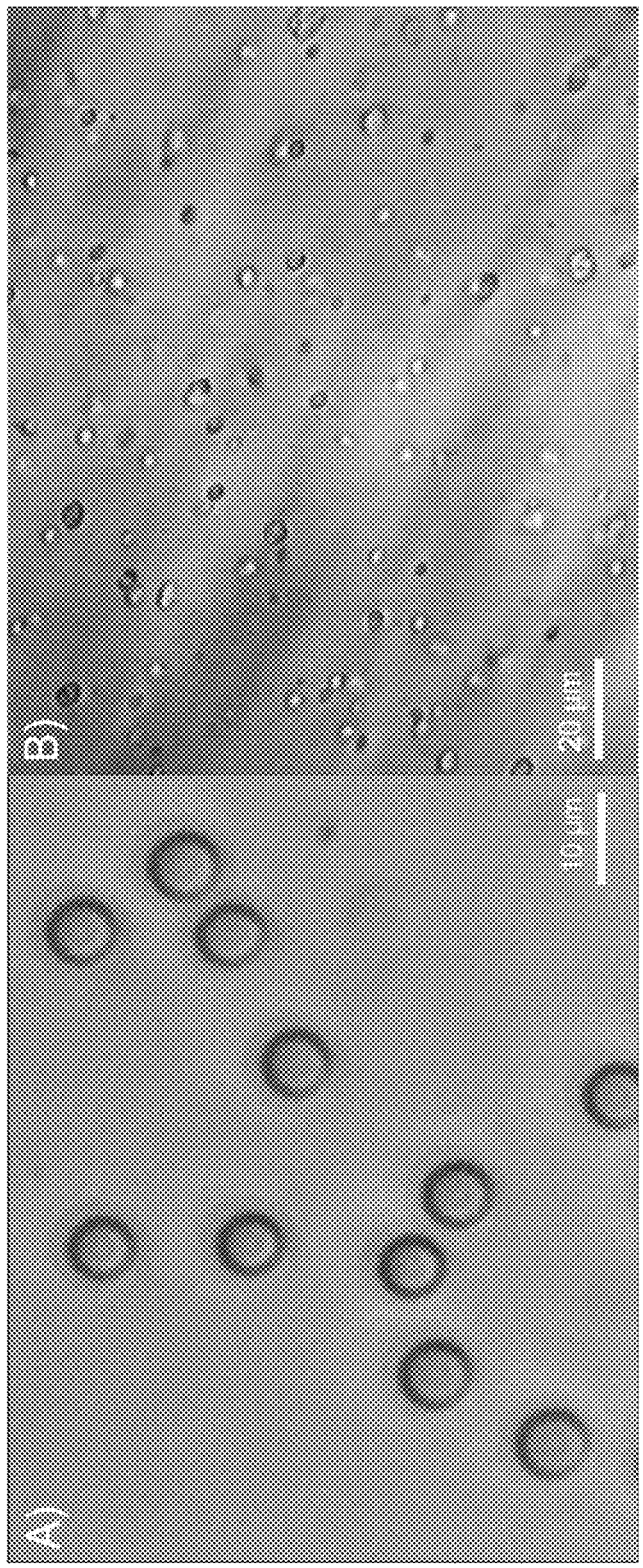
FIGS. 7A-7B. Optical micrograph of RBCs imaged with a 50× objective A) RBCs in NaCl B) RBCs in DSCG.

Imaging healthy RBCs dispersed in isotonic NaCl solutions. FIG. 7A is an optical micrograph of healthy RBCs dispersed in 154 mmol NaCl solutions that are isotonic with the plasma fluid inside the RBCs. Under these conditions, the inventors observed that the RBCs retain their biconcave shape for several hours. FIG. 7B is a micrograph of RBCs dispersed in DSCG. This representative image shows about 60 cells which were analyzed to quantify the asphericity of the cells within the same sample.

Heating of RBC from Nematic to Isotropic phase to observe shape changes of RBCs. DSCG exhibits a complex phase behavior with a co-existence of nematic and isotropic domains for different temperature ranges as a function of concentration. For instance, 17.3 wt % DSCG, upon heating from room temperature (nematic) to 34° C. (bi-phasic region) nucleates domains of the isotropic phase. The RBCs dispersed in the sample were observed to partition into the isotropic tactoids, consistent with past studies that have reported micrometer-meter sized inclusions to elastically strain LCs and thus be ejected from LCs into coexisting isotropic phases. It was observed that RBCs that are initially strained in the nematic phase (25° C.) regain their biconcave shape upon entering into an isotropic phase (39° C.). This observation supports our hypothesis that the changes to the RBC shape are largely governed by the LC elasticity as the osmotic pressure in the thermally equilibrated nematic and isotropic domains of the biphasic region is the same. Heating rate was controlled at 1° C./min.

Figure 8:
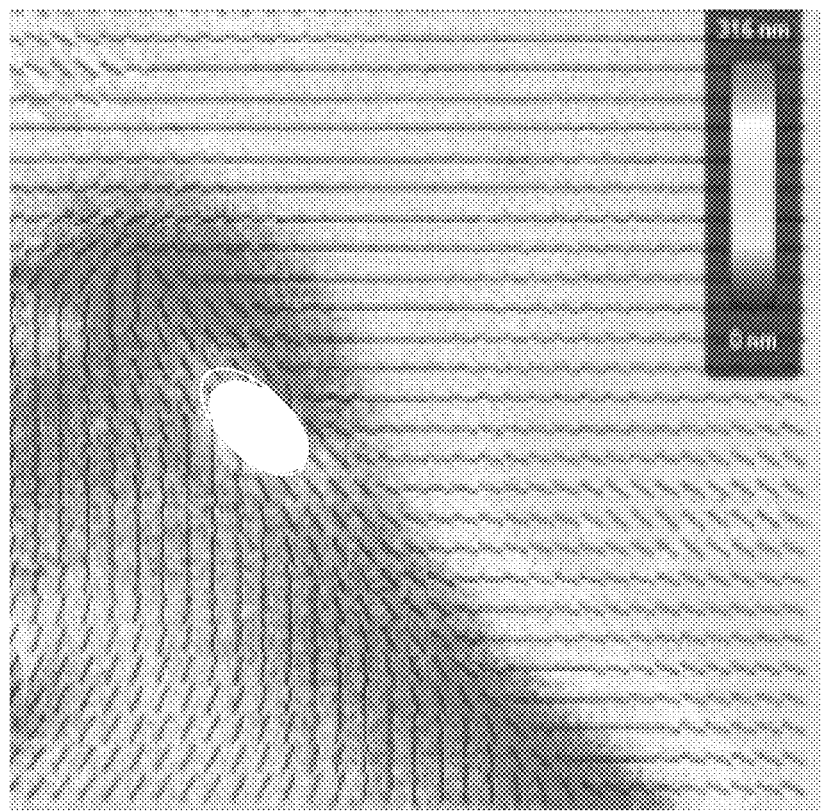
FIG. 8. Polscope map of LC director profile around a RBC.
Figures 9A, 9B, 9C:
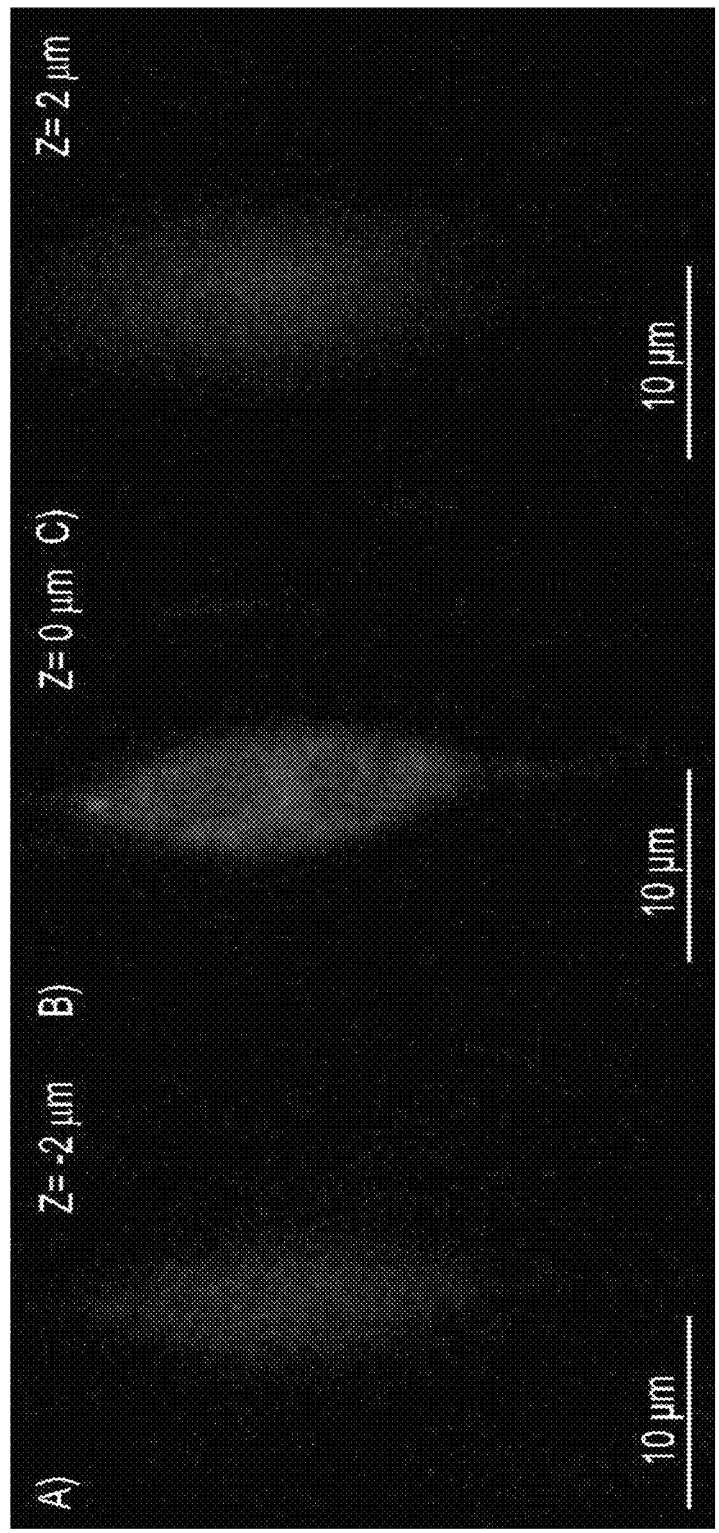
FIGS. 9A-9C. (A)-(C). Confocal fluorescence micrographs at three different z-planes of a strained RBC dispersed in DSCG.

To quantify the orientation of the LC around an individual RBC polscope imaging was performed to supplement the characterization using polarized optical microscopy experiments. Polscope imaging was performed using an Olympus BX41 microscope equipped with a Abrio LC-PolScope package using monochromatic illumination at 640 nm. The white arrow in FIG. 8 shows a +½ defect and the polscope mapping of the director profiles around it. As this director profile is consistent with that around a +½ defect, this feature serves as a confirmation of the fidelity of the mapping of the director profile using the polscope. The director profile around the RBC (shown as white ellipsoid) in FIGS. 9A-9C shows the parallel orientation of the LC around it. Further, the inventors also note that the distortion of the LC director around the RBC is small signifying that the planar anchoring at the interface of the RBC is weak.

Numerical Simulations of shapes of RBCs. The inventors consider a variant of the physical problem at hand and solve numerically for the equilibrium shape of a model red blood cell membrane with a nematic liquid crystal both inside and outside of the cell. The orientational order of the fluid is represented by a second-rank order tensor Q (Landau-de Gennes model), which in a uniaxial system reduces to Q=S (nn−I/3) with S is a scalar order parameter, nn a dyadic product, and I the identity operator. For a uniaxial system the free energy associated with Q is written as a combination of short-range and elastic contributions:

$$\varepsilon(Q) = \int f_a(Q) + f_S(Q) dV \quad (1)$$

Where $$f_S = \frac{A}{2}\left(1 - \frac{U}{3}\right)Q_{kl}Q_{lk} - \frac{AU}{3}Q_{ij}Q_{jk}Q_{ki} + \frac{AU}{4}(Q_{ij}Q_{ji})^2 \quad (2)$$

Here A is an energy scale for the phase transition and U is a dimensionless nematic strength. The scalar order parameter is approximately:

$$S = \frac{1}{4} + \frac{3}{4}\sqrt{1 - \frac{8}{3U}} \quad (3)$$

And the system is in the nematic phase when U>2.8. The elastic energy is given by $$f_S = \frac{L_1}{2}(Q_{ij,k})^2 + \frac{L_2}{2}(Q_{ij,i})^2 + \frac{L_3}{2}Q_{ij}(Q_{kl,i}Q_{kl,j}) \quad (4)$$

Where in terms of the Frank constants $\{K_1, K_2, K_3\}$, then $L_1=(3K_2-K_1+K_3)/6S^2$, $L_2=(K_1-K_2)/S^2$ and $L_3=(K_3-K_1)/2S^2$.

The surface energy of the red blood cell was modeled using the Skalak model. For a reference configuration the inventors take the initial shape described by X and current configuration x(X,t) at time t, the inventors define the surface deformation tensor $$F = (I - nn) \cdot \frac{\partial x}{\partial X} \cdot (I - NN) \quad (5)$$

Where N is the outward pointing normal in the reference configuration and n is the same but in the current configuration and n is the same but in the current configuration and $b = F \cdot F^T$ is the symmetric surface left Cauchy-Green strain tensor. The invariants of this tensor are:

$$I_1 = \lambda_1^2 + \lambda_2^2 - 2 \quad (6)$$

$$I_2 = \lambda_1^2 \lambda_2^2 - 1 \quad (7)$$

The inventors now turn to the energetic penalty for any such deformations. The Skalak strain energy of a surface element dS is given by:

$$W dS = \left(\frac{E_S}{4}[I_1^2 + 2I_1 - 2I_2] + \frac{E_D}{8}I_2^2\right) dS \quad (8)$$

Where $E_S$ and $E_D$ are the elastic shear and dilational moduli, respectively, and have units of energy per area. The in-plane Cauchy stress tensor is given by:

$$\tau = \frac{2}{\lambda_1 \lambda_2} \frac{\partial W}{\partial I_1} + 2\lambda_1 \lambda_2 \frac{\partial W}{\partial I_2}(I - nn) = \quad (9)$$

$$\frac{E_S}{2J}(I_1 + 1)b + \frac{J}{2}(E_D I_2 - E_S)(I - nn)$$

Where $J = \lambda_1 \lambda_2$ measures the local area dilation. The inventors take $E_S = 4*10^{-6}$ N/m and $E_D = 16 E_S$. The surface density is then found by variation, $$f(x \mid X, t)) = \frac{\partial W}{\partial x(X, t)} \quad (10)$$

For reference configuration the inventors take the initial biconcave shape described by the equation below. Parametrizing the surface with angles $\chi[-\pi/2, \pi/2)$ and $\varphi\{0, 2\pi)$:

$$X(x, \varphi) =$$
$$R\sin\chi\cos\varphi + R\sin\chi\sin\varphi + \frac{R}{2}(.207 + 2.003\sin^2\chi - 1.123\sin^4\chi)\cos\chi\hat{Z}$$

where R is the cell radius. To provide uniform spatial coverage the inventors use Distmesh to generate a triangulated mesh of surface above. Numerically, the inventors use the deformation of each triangular element to extract the surface deformation gradient tensor and the principal stretches $\lambda_1$ and $\lambda_2$ on each triangle. Finite difference approximation of the variation in energy with displacement of each gridpoint is performed to identify the surface force f.

Non-dimensionalization. Scaling lengths upon the characteristic semi-major axis length of a red blood cell, R, and forces on $L_1$, the dimensionless molecular field is given by:

$$H_{ij} = -\partial_k \partial_k Q_{ij} - \overline{L}_2[\partial_k \partial_i Q_{kj}] + \beta^2\left(1 - \frac{U}{3}\right)Q_{ij} -$$
$$\beta^2 U\left(Q_{ik} Q_{kj} - \frac{1}{3}\delta_{ij}Q_{kl}Q_{kl} - Q_{ij}Q_{kl}Q_{kl}\right) + \overline{J}S[S^*[Q_{ij}] - Q_{ij}^0]$$

Here the inventors have also defined the nematic coherence length $\xi_N = (L_1/A)^{1/2}$ and the extrapolation length $\xi_S = L_1/J$. Typical values for the bulk free energy parameters in DSCG are given by $A=400$ J/m³ (incidentally, two orders of magnitude smaller than for 5CB, which is 10-5 J/m³, $L_1 = 10^{-11}$ J m⁻¹, and $L_2 = L_1/10$ (Tortora L & Lavrentovich OD (2011), *PNAS*, 108(13):5163.). Experimental values for J vary widely, from $10^{-7}$ to $10^{-2}$ J/m² [Zhou S, et al. (2014) *Soft Matter* 10(34):6571-6581]. With a blood cell radius of approximately R=4 μm, the inventors compute β=50, $L_2$=0.1, and J is in the range 0.08 to 8000. The nematic coherence and extrapolation lengths are roughly $\xi_N$=160 nm and $\xi_S$ ranges from 1 nm to 100 μm. For the remainder of the paper the inventors fix the nematic strength to U=6 (S=0:81), placing the director field deep into the nematic phase, and $L_2$=0.1.

Here the inventors have also defined the nematic coherence length $\xi_N = (L_1/A)^{1/2}$ and the extrapolation length $\xi_S = L_1/J$. Typical values for the bulk free energy parameters in DSCG are given by $A=400$ J/m³ (incidentally, two orders of magnitude smaller than for 5CB, which is 10-5 J/m³, $L_1 = 10^{-11}$ J m⁻¹, and $L_2 = L_1/10$. Experimental values for J vary widely, from $10^{-7}$ to $10^{-2}$ J/m². With a blood cell radius of approximately R=4 µm, the inventors compute β=50, $L_2$=0.1, and J is in the range 0.08 to 8000. The nematic coherence and extrapolation lengths are roughly $\delta_N$=160 nm and $\xi_S$ ranges from 1 nm to 100 µm. For the remainder of the disclosure the inventors fix the nematic strength to U=6 (and by Eq. (3), S=0:81), placing the director field deep into the nematic phase, and $L_2$=0.1. d.

Figure 10:
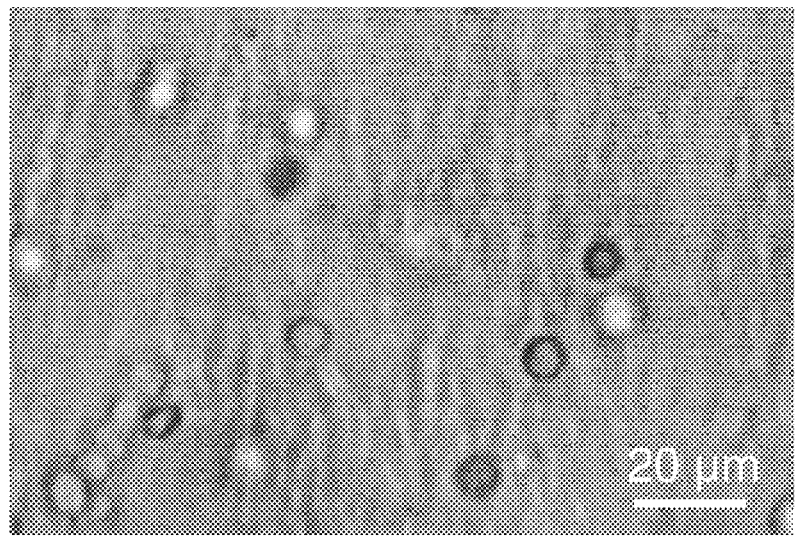
FIG. 10. RBCs crosslinked with glutraldehyde and re-dispsersed in DSCG.

RBCs crosslinked with Glutaraldehyde. FIG. 10 shows RBCs that were crosslinked with glutaraldehyde and re-dispersed in DSCG. Unlike healthy RBCs, no shape transformations are observed for crosslinked RBCs that were induced by the elasticity of the LC.

Figures 11A, 11B:
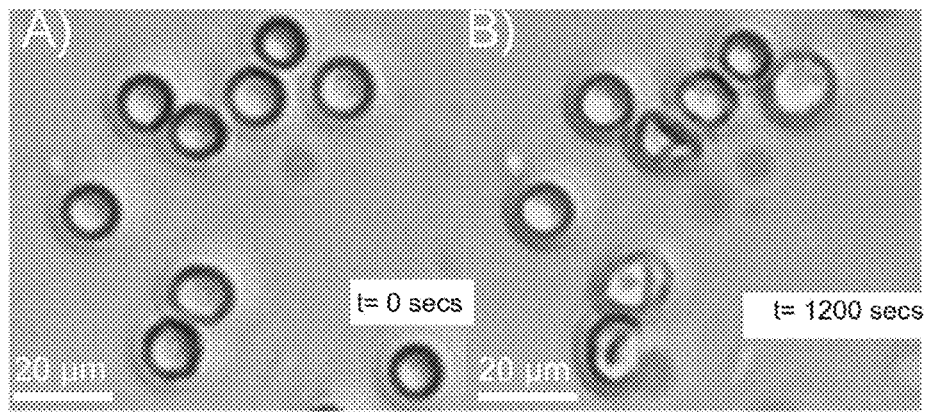
FIGS. 11A-11B. (A) Optical micrograph showing biconcave shape of RBC immediately upon dispersion into isotropic phase of 17.3 wt % DSCG at temperature of 39° C. (B) Shriveled shapes of RBCs after 600 secs.

Shriveling of RBCs in the isotropic phase. It was observed that upon heating a 17.3% wt DSCG solution into its isotropic phase (T>39° C.), the dispersed RBCs shriveled after 20 minutes as shown in FIG. 11B. This observation is consistent with the behavior of RBCs dispersed in hypertonic solutions.

Example 2

The approach of this disclosure builds from the inventors' recent discovery that micrometer-sized giant unilamellar vesicles (GUVs) can be dispersed and strained in water-based liquid crystalline phases, so called lyotropic chromonic LCs (Mushenheim P C et al., (2016), *Proc. Natl. Acad. Sci. U.S.A* 113(20):5564-5569) formed from disodium chromoglycate (DSCG). The DSCG molecules stack into anisometric columnar assemblies, via π-π interactions of their polyaromatic cores (FIG. 1A), which in turn exhibit long-range orientational order and give rise to mesophases with anisotropic elastic properties (Lydon J (2010) *J. Mater. Chem.* 20:10071-10099; Davidson Z S, et al. (2015) *Phys. Rev. E* 91(5):050501; Tortora L & Lavrentovich OD (2011), *PNAS* 108(13):5163; Zhou S, et al. (2014) *Soft Matter* 10(34):6571-6581; Nayani K, et al. (2015) *Nat. Commun.* 6:8067). The inventors' past studies with GUVs were performed by preparing isotropic aqueous phases of DSCG at 45° C. and hydrating spherical GUVs of phospholipids within these solutions (Mushenheim P C et al., (2016), *Proc. Natl. Acad. Sci. U.S.A* 113(20):5564-5569). Upon subsequent thermal quenching to room temperature, nematic LC phases formed within and outside the GUVs, elastically strain the GUVs into spindle-like shapes. Significantly, because the LC is present both inside and outside the GUVs, the osmotic pressure was necessarily balanced across the GUV membranes, and the shape-response of the GUVs was driven by the elastic properties of the LC. The study revealed that small GUVs were strained to the point of transient poration of their membranes, resulting in a flux of nematic DSCG across the GUV membrane (and change in interior volume of the GUV) (Mushenheim P C et al., (2016), *Proc. Natl. Acad. Sci. U.S.A* 113(20):5564-5569).

At the outset of the study reported in this disclosure, it was not obvious to the inventors that it would be possible to strain RBCs using LCs. Unlike the inventors' past experiments with GUVs, where the LC was within and outside the GUVs, the relative osmotic pressures of LC phases and interior of a RBC were unknown. In comparison to GUVs of synthetic phospholipids, RBCs also possess a far more complex organization; the cells comprise an aqueous interior that is concentrated in proteins (largely hemoglobin) with an osmotic pressure of 280 mosm/kg; the cell membrane comprises a mixture of phospholipids, cholesterol and trans-membrane proteins (glycocalyx), with a network of proteins located on the inner surface of the lipid bilayer (spectrin) (Litster J D (1975) *Physics Letters A* 53(3):193-194; Peng Z L, et al. (2013) *PNAS* 110(33):13356-13361; Pivkin I V & Karniadakis G E (2008) *Phys. Rev. Lett.* 101(11):118105; Puig-De-Morales-Marinkovic M et al., (2007) *Am. J. Physiol.-Cell Physiol.* 293(2):C597-C605). Human RBCs typically possess a complex biconcave shape that reflects the presence of excess membrane area (relative to volume) to enable efficient gas (oxygen) exchange, although other mammals possess RBCs with other distinct shapes (Peng Z L, et al. (2013) *PNAS* 110(33):13356-13361; Pivkin I V & Karniadakis G E (2008) *Phys. Rev. Lett.* 101(11):118105; Puig-De-Morales-Marinkovic M et al., (2007) *Am. J. Physiol.-Cell Physiol.* 293(2):C597-C605; Fedosov D A et al, (2010), *Biophys. J.* 98(10):2215-2225; Rudenko S V et al., (1998), *Biochem.-Moscow* 63(12):1385-1394; Svoboda K et al., (1992), *Biophys. J.* 63(3):784-793).

Past studies have shown that the bending and the area modulus of RBC membranes can be described as $k_b=Yh^3/12$ and $k_a=Yh$, respectively, where $k_b$, $k_a$, Y and h are the bending modulus, area modulus, Young's modulus and the thickness of the membrane, respectively (Deserno M (2015), *Chemistry and Physics of Lipids* 185:11-45). For a 5 nm-thick bilayer, the inventors estimate the bending and area modulus to be about 50 kT and 60 mN/m, respectively, consistent with other experimental studies (Engelhardt H & Sackmann E (1988), *Biophys. J.* 54(3):495-508). Because LCs have elastic constants (K) of the order of 10 pN, the energetic cost of deforming LCs around a RBC (~8 µm) is estimated to be ~104 kT (K*R, where K is elastic constant of the LC and R~10 µm), which the inventors hypothesized would be sufficiently large to strain RBCs via bending modes (~$k_b$ (1/a*1/R)*R^2~(kb R)/a~200 kT) of deformation, where the bending cost is estimated by assuming 1/a and 1/R to be the radii of curvature at a given surface location of the RBC.

In addition to providing fundamental insight into the physics of deformation of soft colloids in LCs, our study hints at the basis of a new approach for rapid characterization of the mechanical properties of RBCs and other biological cells (BarthÈS-Biesel D, Diaz A, & Dhenin E (2002), *J. Fluid Mech.* 460:211-222). Computational models of shape-responses of RBCs to applied strain have revealed transitions to "bullet-like" cell shapes with a central fold and then "parachute-like" shapes. A key feature of all these theoretical predictions is that the strained RBCs retain a fold along the long axis of the cell. In contrast, unambiguous evidence of the presence of folded shapes is not found in prior experiments, including those involving optical tweezers or applied electric fields (Engelhardt H & Sackmann E (1988), *Biophys. J.* 54(3):495-508; Dao M, Lim C T, & Suresh S (2003), *J. of the Mech. and Phys. of Solids* 51(11):2259-2280).

Techniques such as magnetic bead actuation, atomic force microscopy (AFM), and micropipette aspiration have been used previously to strain RBCs and to characterize their mechanical properties. However, all of these techniques apply local deformations of RBCs (the region of the RBC that is strained is small compared to the size of the cell (Peng Z L, et al. (2013) *PNAS* 110(33):13356-13361; Puig-De-Morales-Marinkovic M et al., (2007) *Am. J. Physiol.-Cell Physiol.* 293(2):C597-C605; Svoboda K et al., (1992), Biophys. J. 63(3):784-793). For instance, the area dilation modulus of RBCs can be extracted using the micropipette aspiration technique, but membrane folding can lead to inaccurate measurement because the technique is not based on global changes to RBC shape (Engström KG & Meiselman H J (1996), *Cytometry* 23(1):22-27). The inventors also note that the experimental methods reported herein for studying mechanical properties of RBCs do not require complex instrumentation (Bao G & Suresh S (2003), *Nat. Mater.* 2(11):715-725, Peng Z L, et al. (2013) *PNAS* 110 (33):13356-13361, Puig-De-Morales-Marinkovic M et al., (2007) *Am. J. Physiol.-Cell Physiol.* 293(2):C597-C605; Dao M, Lim C T, & Suresh S (2003), *J. of the Mech. and Phys. of Solids* 51(11):2259-2280) and permit parallel characterization of the mechanical properties of individual cells within a population, thus providing insight into heterogeneity in the population.

The results described in this disclosure test the hypothesis that liquid crystals (LCs) can be used to globally strain RBCs, and that cells with distinct mechanical properties exhibit distinct shape-responses to the mechanical environment defined by the LC. In addition, the present disclosure also provides insight into previously unexplored questions such as: 1) Is it possible identify synthetic aqueous-LC phases that are isosmotic with the interior of mammalian cells? 2) Can imaging of LCs be used to rapidly characterize heterogeneities in cell populations at an individual cell level? 3) Can relevant mechanical properties of cells, such as their bending and area moduli, be extracted from LC-driven shape changes of RBCs?

Example 3: Preparing LC Phases that are in Osmotic Equilibrium with Cells

Figures 2A, 2B, 2C, 2D:
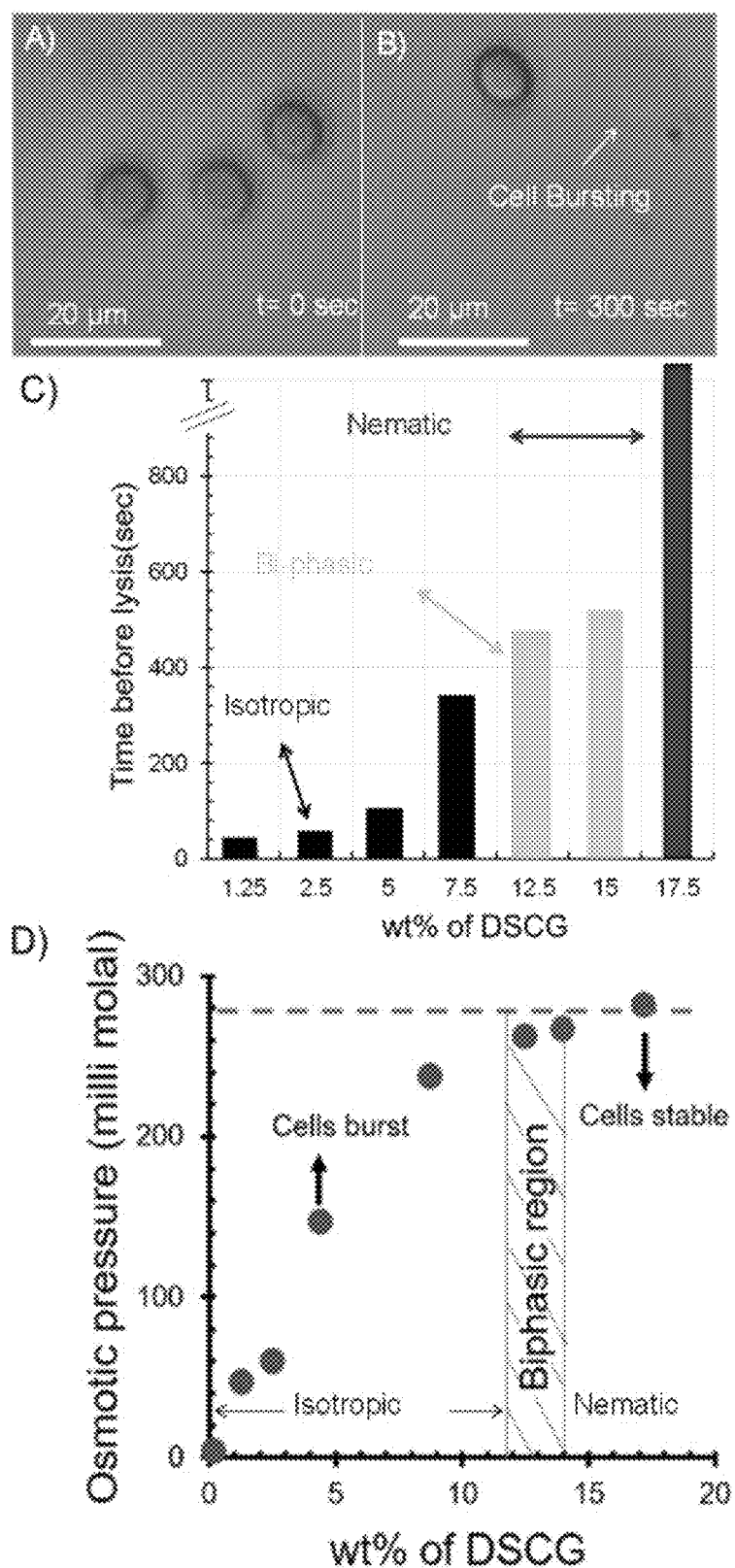
FIGS. 2A-2D. (A) and (B) RBCs imaged (optically) immediately (A) and 300 s (B) after transfer to an aqueous DSCG solution (154 mM). The RBCs are sedimented onto a glass substrate and thus the disk shapes observed in the images are projections of the biconcave shape. (C) Time for lysis of RBCs suspended in aqueous DSCG solutions plotted as a function of the concentration of DSCG. The black, yellow and blue colors indicate isotropic, biphasic and nematic concentrations of DSCG. (D) Osmotic pressure (measured using vapor pressure osmometry) of aqueous DSCG solutions.

The initial experiments were performed to determine whether or not it is possible to prepare LC phases from DSCG that are in osmotic equilibrium with the interior of a RBC. As noted above, the osmotic pressure of the interior of a RBC is 280 mosm/kg, which is equivalent to (isotonic) with an aqueous solution containing 154 mM NaCl (Canham P B & Parkinson D R (1970), *J. Physiol. Pharmacol.* 48(6):369-376; Koslov M M & Markin V S (1984), *J. of Theoretical Bio.* 109(1):17-39; Ohno M et al., (2009), *Langmuir* 25(19):11680-11685). Initially, the inventors suspended RBCs in 154 mM NaCl and confirmed that the RBCs maintained their biconcave shapes for a period of several hours (FIG. 2A and FIG. 7A). In contrast, when RBCs were suspended in aqueous solutions containing 154 mM DSCG (pH 8.4), which corresponds to an isotropic phase of DSCG, the inventors observed RBCs to swell from an initially biconcave shape (FIG. 2A) and burst over a period of ~300 s (FIG. 2B). This result is consistent with the 154 mM DSCG solution being hypotonic relative to the interior of RBC, resulting in a flux of water into the RBC and cell lysis (Canham P B & Parkinson D R (1970), *J. Physiol. Pharmacol.* 48(6):369-376; Koslov M M & Markin V S (1984), *J. of Theoretical Bio.* 109(1):17-39; Hasler C R et al., (1998) *Nephrol. Dial. Transplant.* 13(12):3132-3137). The inventors found, however, that the average lifetimes of the RBCs prior to lysis increased monotonically with concentration of DSCG (FIG. 2C). Significantly, when using 17.3 wt % of DSCG (588 mM), which corresponds to a nematic LC phase of DSCG at 25° C. (FIG. 2C), RBCs did not lyse over durations of several hours. This result led us to hypothesize that osmotic equilibrium between the interior of the RBC and the LC was achieved under these conditions. To quantify the osmotic pressure of the DSCG solutions, the inventors independently measured the vapor pressures of DSCG solutions (FIG. 2D). Inspection of FIG. 2D reveals that aqueous of 17.3 wt % DSCG is indeed isotonic with the interior of RBCs (red dashed line in FIG. 2D), whereas lower concentrations of DSCG, including 154 mM DSCG (FIGS. 2A and 2B), are hypotonic. The inventors note that the RBCs imaged in FIGS. 2A-2D had sedimented onto a lower substrate and thus a consistent projection of the biconcave shape was observed.

The finding that aqueous LCs formed from 17.3 wt % DSCG are isotonic with the interiors of RBCs allowed the inventors to perform experiments that explored the mechanical interactions of LCs and RBCs. Specifically, the inventors used an isotonic LC to ensure that RBC shape changes induced by the elasticity of the LC phase (see below) are not convolved with shape changes arising from a flux of water across the RBC cell membrane (Rudenko S V et al., (1998), *Biochem.-Moscow* 63(12):1385-1394; Sheetz M P et al. (1976), *J. Cell Biol.* 70(1):193-203). The inventors envisage, however, that an imbalance in osmotic pressure can be exploited in future studies to swell or shrink RBCs to provide additional insight into biomechanical properties of the cells.

Example 4

Figures 3A, 3B, 3C, 3D, 3E, 3F:
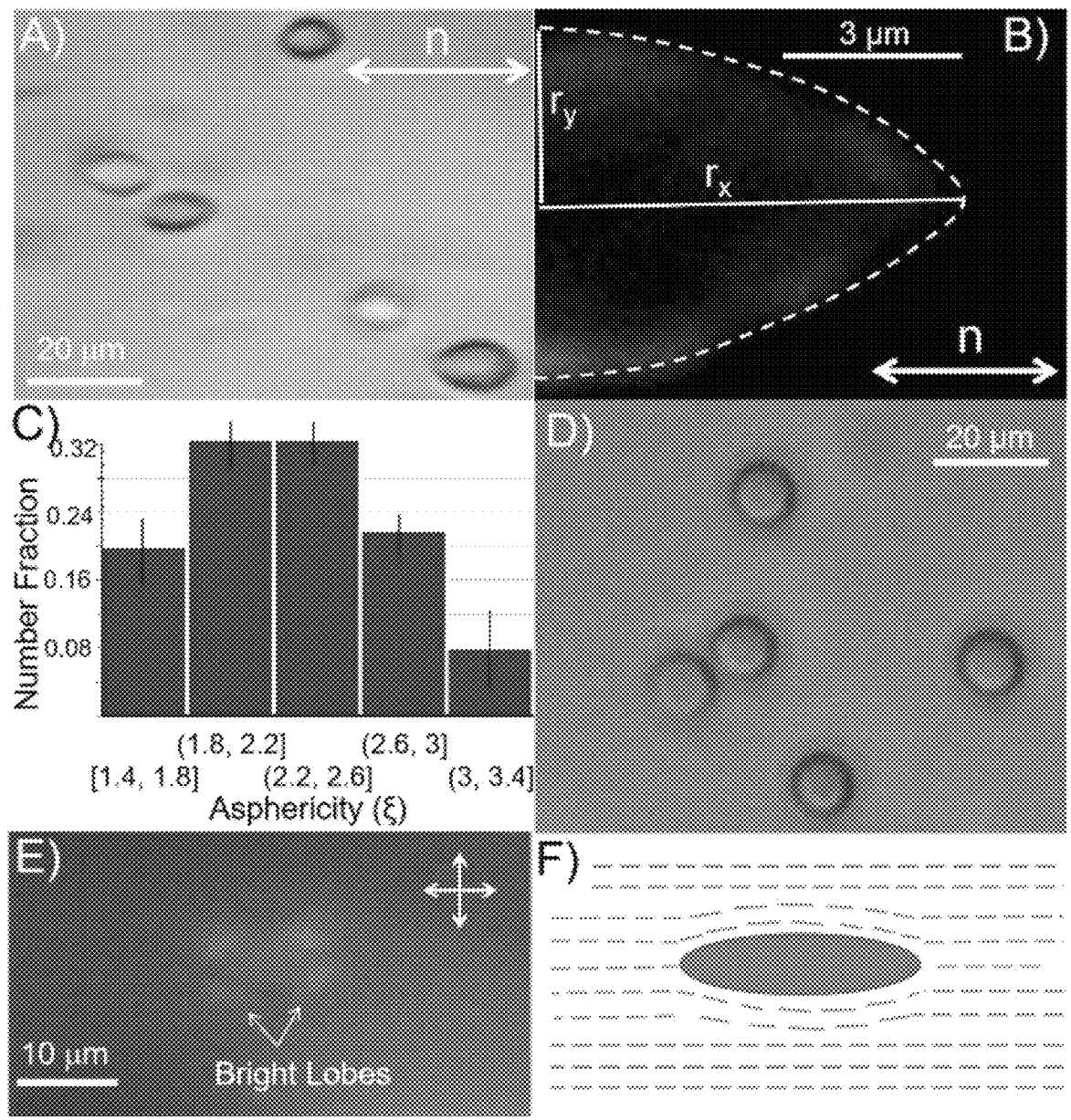
FIGS. 3A-3F. (A) Optical micrograph of strained RBCs suspended in 17.3 wt % DSCG aqueous solution at 25° C. The far-field director of the LC formed by the DSCG is shown by the white arrow (B) Confocal micrograph of strained RBC dispersed in DSCG (C) Histogram of heterogeneity of $\xi$ for 120 RBCs strained by DSCG (D) Optical micrograph of sample in (A) following heating of the DSCG into the isotropic phase (39° C.) (E) Optical micrograph showing the texture of DSCG around a RBC (F) Schematic illustration of the LC orientation around a RBC.

In contrast to the biconcave shapes of RBCs observed in isotonic NaCl solutions (FIG. 2A), FIG. 3A shows optical micrographs of RBCs suspended in 17.3 wt % DSCG at 25° C. Inspection of FIG. 3A reveals that the RBCs in the nematic phase of DSCG assumed anisometric shapes with their major axes aligned parallel to the far-field orientation of the LC (white arrow in FIG. 3A). To further characterize the shapes of the RBCs in nematic DSCG, confocal fluorescence scanning microscopy of strained RBCs was performed. The RBCs were dispersed in isotonic NaCl solutions and treated with a membrane staining dye (DiD) at concentrations of 15 µM for a period of 3 hrs (Rappaz B, et al. (2008), *Cytometry Part A* 73A(10):895-903). Stained cells were then ultra-centrifuged and washed in isotonic NaCl solutions twice before dispersing them in DSCG solutions. Consistent with brightfield optical microscopy images in FIG. 3A, the confocal images shown in FIG. 3B reveal the RBC to be strained into anisometric shapes that are aligned along the far-field orientation of the LC. FIG. 3B also shows an ellipsoidal fit to the shape of a strained RBCs leading to quantification of the long ($r_x$) and minor axis ($r_y$) of the RBC in the plane of the LC director (X-Y plane). The measured in-plane (of the LC director) aspect ratios ($=r_x/r_y$), as shown in FIG. 3C for over 200 strained RBCs, are polydisperse, ranging from 1.4 to 3.2 with a high variance of 0.36. In contrast, the equivalent aspect ratios of RBCs prior to straining are relatively monodisperse with $r_x/r_y$ 1.04±0.07 (FIG. 7A). These results contrast to past experiments on GUVs strained in LCs wherein the inventors did not observe a polydispersity in the values of $r_x/r_y$ (Mushenheim P C et al., (2016), *Proc. Natl. Acad. Sci. U.S.A* 113(20):5564-5569). The emergence of the broad distribution in values of $r_x/r_y$ of the strained RBCs unmasks the heterogeneity in mechanical properties of the populations of RBCs. The inventors also note that our methodology enables the parallel determination of the aspect ratios of individual cells within a population. For instance, FIG. 3A is a cropped image (showing 5 strained cells) of a representative optical micrograph used to determine the aspect ratios of over 60 RBCs from a single image (FIG. 7B).

Upon heating the aqueous LC to form an isotropic phase (to 39° C. at 2° C./min), the inventors observed the RBCs to reform their characteristic biconcave shape (FIG. 3D) within a few seconds of the phase transition into the isotropic phase. By observing the textures of the LC around a RBC as shown in FIG. 3E and characteristic textures of the bright regions at angles approximately 45° to the polarizers, the inventors are able to confirm that the LC has a parallel anchoring at the interface of a RBC. This observation was confirmed through Polscope mapping of the orientation of the LC director around a RBC, as shown in FIG. 8. A schematic depicting the orientation of the LC around a RBC is shown in FIG. 3F.

Figures 4A, 4B, 4C, 4D:
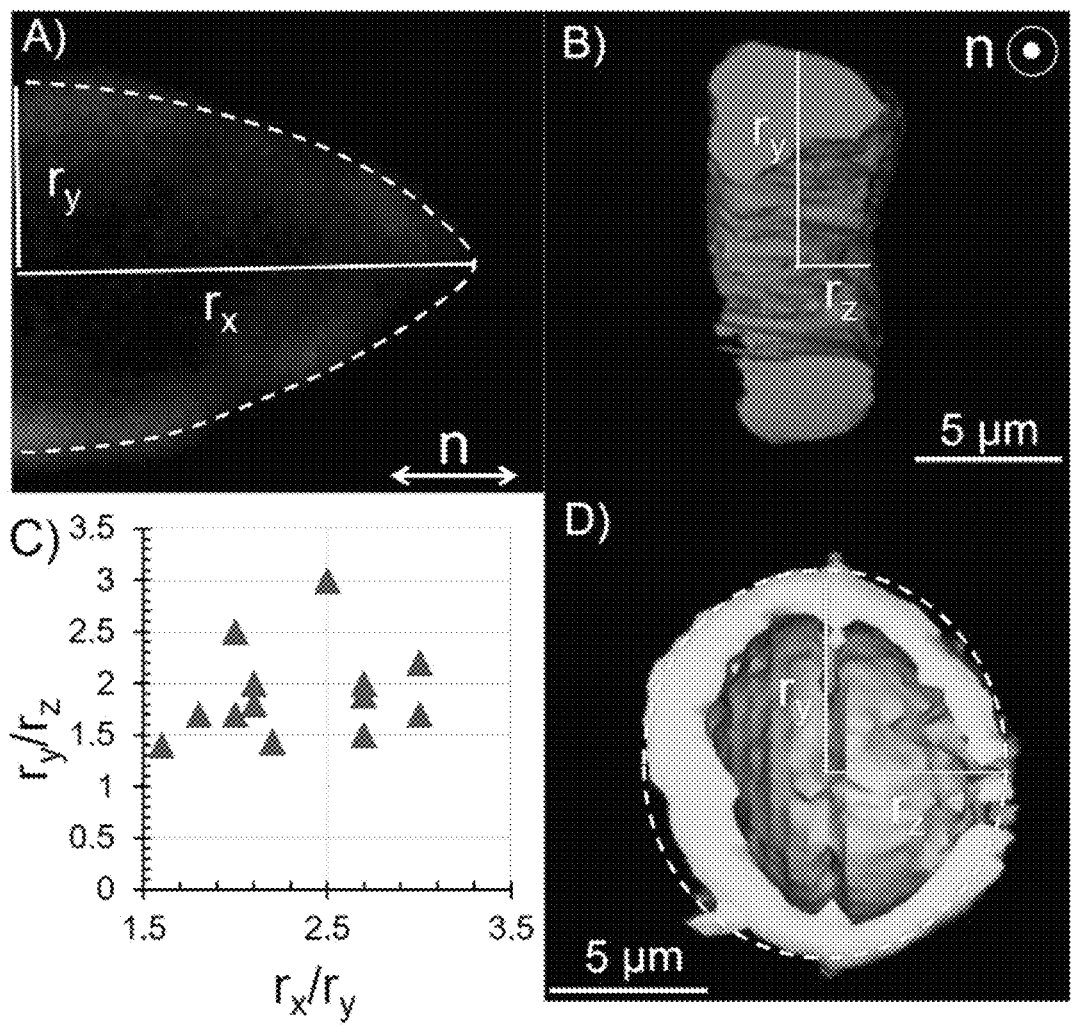
FIGS. 4A-4D. (A) End-on view of the 3-D rendering of confocal z-stacks of strained RBCs (B) Y-Z cross-section of a RBC strained by DSCG obtained through confocal imaging (C) $r_x/r_z$ as a function of $r_x/r_y$. (D) Y-Z cross-section of a GUV strained by DSCG obtained through confocal imaging.

The LC-driven, three-dimensional shape transformations of the RBCs, as shown in FIGS. 3A and 3B, are substantially more complex than the inventors' past studies of stretching a spherical GUV into an axisymmetric spindle shape by a LC (Mushenheim P C et al., (2016), *Proc. Natl. Acad. Sci. U.S.A* 113(20):5564-5569). Specifically, a biconcave RBC has a line of symmetry that is perpendicular to the predicted principal direction of strain in the nematic LC phase. This leads to an intricate interplay between the LC-elasticity and curvature elasticity of the RBC membrane (Pivkin I V & Karniadakis G E (2008) *Phys. Rev. Lett.* 101(11):118105; Deschamps J et al., (2009), *PNAS*, 106(28):11444-11447), with the potential to lead to highly irregular shapes under strain. 3-D reconstruction of z-stacks of the confocal fluorescence images in FIG. 4A and FIGS. 9A-9C reveals that ends of the RBCs do not converge to a point. This is a significant departure from the inventors' prior work on GUVs dispersed in LCs in which the inventors observed GUVs to assume spindle-like shapes with pointed ends. More strikingly, the 2-D cross-sections (X-Y and Z-Y planes) of strained RBCs (LC director is along the x-axis) revealed that the dimensions of the RBCs in the Y ($r_y$) and Z ($r_z$) directions differ, as shown in FIG. 4B. The inventors hypothesize that the anisometric shape of RBCs in the Y-Z plane is a consequence of the initial biconcave nature of the RBC (the initial cell-length along the Z-axis of the RBC is 2 μm and 8 μm along the X and Y axes). The inventors quantify $r_y/r_z$ as a function of $r_x/r_y$ in FIG. 4C. The inventors note that, although $r_x/r_y$ (variance=0.36) varies substantially between cells, as quantified in FIG. 3C, $r_y/r_z$ (variance=0.04) is characterized by a narrower distribution (1.9±0.2). The inventors provide additional insight into the narrow distribution of values of $r_y/r_z$ below by using both high-magnification optical imaging and numerical simulations. As a control experiment, FIG. 4D shows a Y-Z cross-section of a strained GUV, revealing the expected circular cross-section.

Example 5

Figures 5A, 5B, 5C, 5D, 5E, 5F:
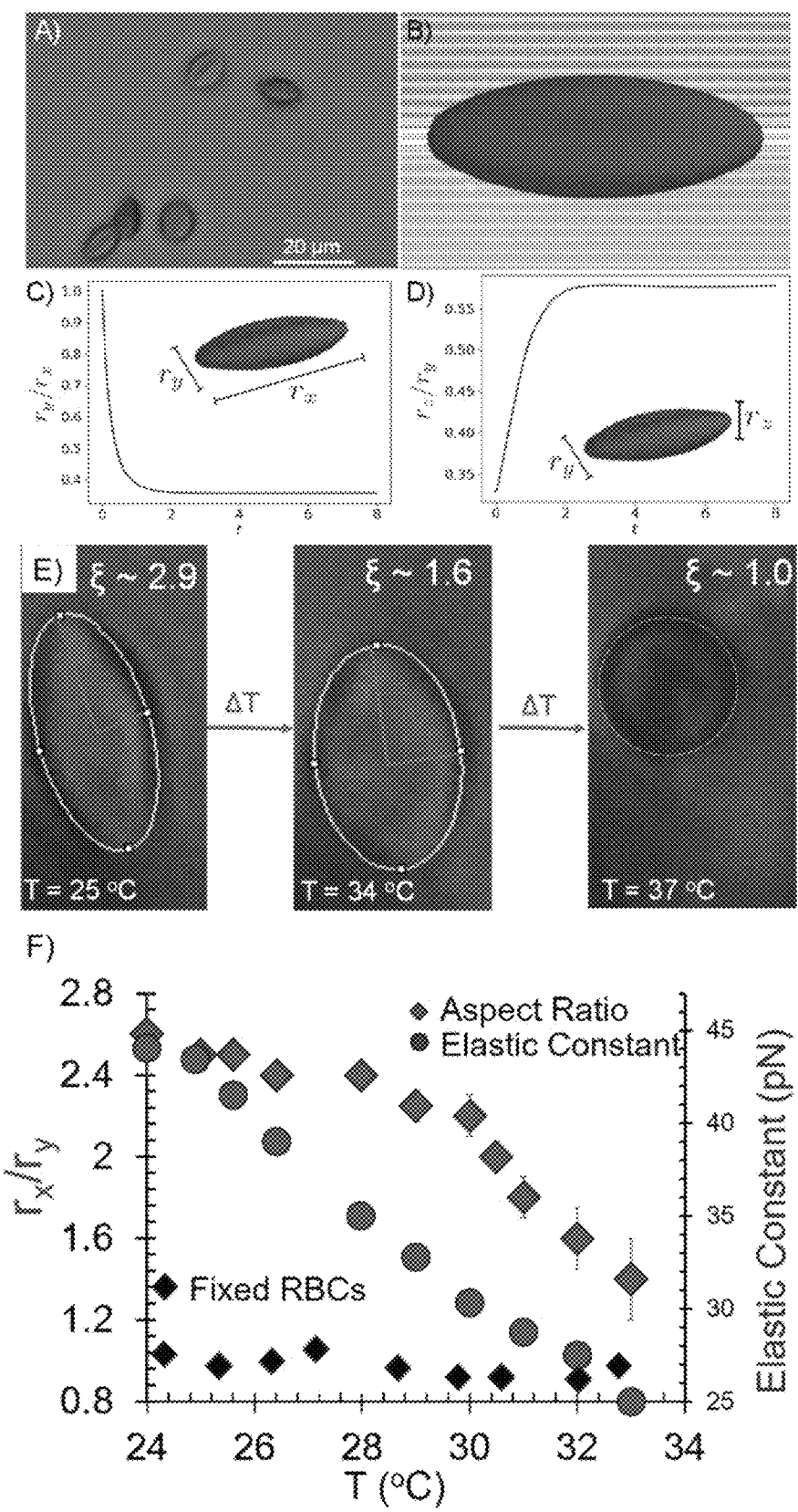
FIGS. 5A-5F. (A) Optical micrographs of crosslinked RBCs that were initially strained in DSCG imaged with a 63× objective. (B) Simulation of strained RBC. (C) Evolution of $r_x/r_y$ to its equilibrium value (D) Evolution of $r_y/r_z$ to its equilibrium value (E) Optical micrographs showing the change in $r_x/r_y$ of RBC as a function of temperature. Scale bar is 3 μm (F) Plots of $r_x/r_y$ of healthy and fixed RBC plotted as a function of temperature. The variation of the elastic constants (blue dots) with temperature is shown in the same plot.

Next, the inventors sought to determine if the initial biconcave shape of the RBC and the associated memory of this shape by the spectrin network, impact the strained shapes adopted by RBCs (i.e., $r_y/r_z$~1.9). The optical imaging described above was performed in DSCG, within which the scattering of light, due to dynamic LC director fluctuations, impacted efforts to obtain high resolution optical micrographs of the RBCs. To obtain high resolution images in water, the inventors strained RBCs in DSCG and then treated the cells with 0.1 vol % of glutaraldehyde for two hours. Glutaraldehyde has been shown previously to crosslink the hemoglobin inside the RBC, which led the inventors to hypothesize that crosslinked RBCs may retain their LC-strained shapes even upon the removal of the elastic strain. The crosslinked RBCs were then ultra-centrifuged, rinsed three times with DI water, and imaged under brightfield illumination conditions (FIG. 5A). Inspection of the optical micrograph in FIG. 5A reveals the presence of a fold along the mid-plane of the strained RBC. The fold, which is evident in all RBCs in FIG. 5A (independent of $r_x/r_y$), provides insight into why $r_y/r_z$ is observed to assume a value of ~2: the Y-Z cross-section of the strained shape of the RBC can be approximated as two cylinders separated by the fold.

To provide additional insight into the mechanical response of the RBCs to the LC, the inventors modeled numerically the equilibrium shape of a red blood cell membrane immersed in LC. The inventors aimed to use the simulations to interpret the experimental measurements of the LC-induced shape-changes in the RBCs in terms of mechanical properties of the RBCs. The inventors also aimed to identify key RBC shape metrics that can be rapidly measured during experiment to quantify RBC mechanical properties.

Key non-dimensional groups in the computation include; $\beta=R/\xi_N$, where R is the semi-major axis of the RBC and is the $\xi_N$ nematic correlation length; $J=R/\xi_S$, where $\xi_S$ is the extrapolation length and $\overline{L_2}=L_2/L_1$, where $L_1$ and $L_2$ are the first and coefficients of the expansion of the Landau-de-Gennes free energy of the LC. Scaling the lengths with the R and the forces with $L_1$, the dimensionless molecular field describing the LC elasticity is given by:

$$H_{ij} = -\partial_k \partial_k Q_{ij} - \overline{L_2}[\partial_k \partial_l Q_{kj}] + \beta^2\left(1 - \frac{U}{3}\right)Q_{ij} - \qquad (1)$$

$$\beta^2 U\left(Q_{ik}Q_{kj} - \frac{1}{3}\delta_{ij}Q_{kl}Q_{kl} - Q_{ij}Q_{kl}Q_{kl}\right) + \overline{J}S[S^*[Q_{ij}] - Q_{ij}^0]$$

The inventors calculated $\beta$~50, $\overline{L_2}$~0.1 and J~100 from the values of bulk elastic constants and typical anchoring energies for DSCG (Zhou S., et al. (2014), *Soft Matter* 10(34):6571-6581). The strain on the RBC resulting from the elasticity of the LC was modeled as a Skalak strain energy element given by $$W^* dS^* = \left[\frac{E_S^*}{4}(I_1^2 + 2I_1 - 2I_2) + \frac{E_D^*}{8}I_2^2\right]dS^* \qquad (2)$$

where $E_S$ and $E_D$ are the elastic shear and dilation moduli respectively. For the initial simulation, the inventors take $E_S=4*10^{-6}$ N/m and $E_D=10^{-4}$ N/m (Dao M et al., (2003), *J. of the Mech. and Phys. of Solids* 51(11):2259-2280). Further, the inventors also use the experimentally characterized aspect ratios ($r_x/r_y$) to extract $E_S$ and $E_D$ as fitting parameters in our simulations as described below. $I_1$ and $I_2$ are the strain invariants (Skalak R et al., (1973), *Biophysical journal* 13(3):245-264).

An example of the LC-strained RBC shape, as predicted by this simulation, is shown in FIG. 5B. Inspection of FIG. 5B reveals that the simulation predicts a fold along the axis of symmetry of the strained RBC. FIG. 5C reveals that the calculated equilibrium (t>4 secs) value of $r_x/r_y$=2.5 is in good agreement with the experimentally observed values as shown in FIG. 4C (2.3±0.6). Additionally, the calculated ratio $r_y/r_z$, which characterizes the strained RBCs in a plane perpendicular to the director, was 1.9, also in good agreement with the experiments (1.9±0.2). The stiffer RBCs in our experiments, which were strained to $r_x/r_y$~1.7, were calculated to have $E_S$~16*$10^{-6}$ N/m and RBCs that were strained to $r_x/r_y$~3 were estimated to have $E_S$~2*$10^{-6}$ N/m. For values of $E_D=10^{-4}$ N/m and similar, the predicted cell shapes were not dependent on the value of $E_D$ because the cell membranes were effective inextensible.

Example 6

To provide additional evidence that the LC elasticity is responsible for the RBC shape changes described above, the inventors quantified $r_x/r_y$ of strained states of RBCs as a function of temperature of the nematic DSCG phase. Past studies have reported the temperature-dependent elastic properties of DSCG phases (Zhou S, et al. (2014) *Soft Matter* 10(34):6571-6581). The inventors fit the projected shapes of RBCs sedimented onto the surfaces of glass substrates (see FIG. 5E) to the shapes of ellipsoids (ImageJ software). Inspection of FIG. 5E reveals that the asphericity of the shapes of strained RBCs decreased monotonically as a function of increasing temperature becoming unity in the isotropic phase. The inventors compare the temperature-dependent shapes of the RBCs to temperature-dependent changes to the elastic constants of the LC presented with the blue dots in FIG. 5F. These measurements reveal that the change in shape of the RBCs correlates closely with the change in elastic properties of the LCs. In contrast to native RBCs, the inventors measured glutaraldehyde-treated (and hence stiffer) RBCs (with biconcave shape) to not be measurably strained by the elasticity of the LC, as shown in FIG. 5E (black dots in FIG. 5E, images shown in FIG. 10) (Maciaszek J L & Lykotrafitis G (2011), *J. Biomech.* 44(4): 657-661). Furthermore, the RBCs treated with glutaraldehyde (0.1 vol %) maintained their biconcave shape, independent of the temperature of the nematic phase (FIG. 10). RBCs fixed with glutaraldehyde have been used previously to model the mechanical properties of malaria-infected red blood cells (Abay A, et al. (2019), *Front Physiol* 10:514-514). These results provide support for the proposal that LCs can be used to rapidly distinguish healthy and diseased cells at the level of individual cells.

Figures 6A, 6B, 6C, 6D, 6E:
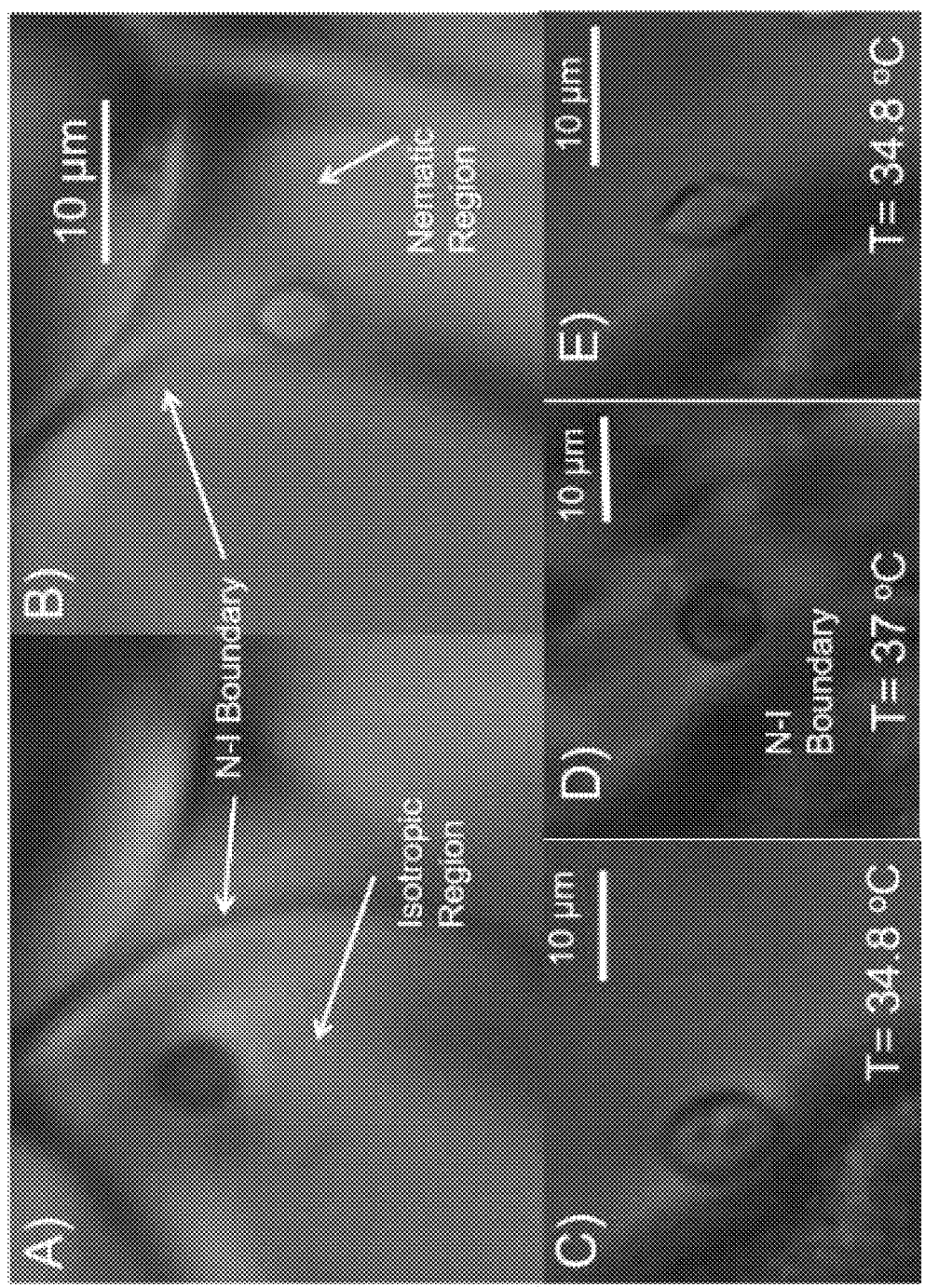
FIGS. 6A-6E. (A) and (B) Optical micrographs showing shapes of RBCs in the isotropic and nematic domains of the biphasic regime of DSCG respectively (C)-(E) Shape changes of RBCs as it is heated from nematic phase in (C) to the biphasic region in (D) where the RBC is inside an isotropic domain. Upon cooling back to the nematic phase the RBC adopts a strained shape in (E) at 34.8° C.

The inventors addressed the reversibility of the RBC shape-response to LC mechanical stresses by observing their RBC shapes as they were exposed to isotropic and nematic domains in the biphasic region of DSCG. For 17.3 wt % DSCG, the biphasic region occurs at temperatures between 35-39° C. In brief, as the inventors heated a sample from room temperature (nematic phase) to a temperature beyond 35° C., the inventors observed tactoids of isotropic phase to nucleate in a continuous nematic phase. The RBCs dispersed in the sample were observed to partition into the isotropic tactoids, consistent with past studies that have reported micrometer-meter sized inclusions to elastically strain LCs and thus be ejected from LCs into coexisting isotropic phases (Kim Y-K et al., (2018), *Nature* 557(7706):539-544). A small change in temperature was observed to result in motion of the nematic-isotropic interface, leading occasionally to the transfer of a RBC from an isotropic region (FIG. 6A, t=0) to a nematic region (FIG. 6B, t=10 sec). In the isotropic region prior to transfer, the RBCs were observed to have biconcave appearances, but upon being engulfed by a nematic region, the RBC were strained into ellipsoid shapes. At equilibrium, the osmotic pressure in coexisting nematic and isotropic phases is equal, thus the results in FIGS. 6A and 6B provide additional support for the inventors' conclusion that the strained shape of the RBC in the nematic region is predominantly due to the elasticity of the LC. Additionally, within the biphasic region, as shown in FIGS. 6B to 6D, it was possible to cycle between a narrow range of temperatures (35° C.-39° C.) and reversibly change the shape of RBC from strained states to biconcave shapes, multiple times as it experienced sequentially nematic and isotropic environments. Specifically, FIG. 6B shows a strained RBC at 34.8° C., which upon heating the sample to 37° C., enters an isotropic domain and regains its biconcave shape. Upon cooling the same sample back to 34.8° C., the RBC is strained again into the elongated shown in FIG. 6D.

A significant finding reported in this paper is that the osmotic pressure of a nematic phase with 17.3 wt % DSCG at room temperature is the same as the interior of a RBC. This finding allowed the inventors to attribute shape changes of RBCs in the nematic phase to elasticity of the LC. However, the inventors note that changes in the shapes of RBCs, for instance in FIGS. 6A and 6B (which are triggered by changes in temperature, must also be accompanied by a small change of osmotic pressure. This is evidenced by the observation that RBCs dispersed in 17.3 wt % DSCG solutions, when heated to 39° C. (an isotropic and hypertonic phase) show evidence of shriveling after 20 minutes (FIGS. 11A-11B). The time-scale (>20 mins) associated with the shriveling of RBCs allows the inventors to eliminate the possibility that the reversible shape changes of RBCs upon cycling between the nematic and isotropic domains, as shown in FIG. 6, are a result of osmotic stresses. The inventors note that shape changes of RBCs (biconcave in isotropic; elongated shapes in nematic) can be observed within a few seconds of the phase transition between the isotropic and LC phases.

Example 7

This disclosure demonstrates that LCs provide the basis of a simple method to strain RBCs, and that distinct mechanical responses are exhibited depending on the stiffness of RBCs. In particular, RBCs fixed with glutaraldehyde, a common model of the mechanical properties of malarial cells, do not show a shape-response to stresses imposed by the LC. In contrast to past techniques for measurement of single cell mechanical properties, our methodology based on LCs enables high-throughput measurements of the changes in the shapes of RBCs and quantify them for individual cells. This allows quantification of the heterogeniety in mechanical properties of cells within populations of RBCs. A key finding that enables this study is the discovery of the inventor that a LC that is isotonic with the interior of a RBC. This enables straining of RBCs via use of mechanical forces generated by LCs, revealing anisometric strained shapes or RBCs that possess a fold along the long axis and a temperature-dependent response of the shapes of RBCs strained by LC elasticity. These results validate the initial hypothesis that LC elasticity can strain the RBC membranes based on the estimates of their bending and area moduli, while also providing unequivocal experimental evidence of the strained shapes of RBCs predicted previously by several theoretical models. In addition, the inventors show that the shape-responses of RBCs can be modulated as a function of temperature, consistent with the change in the elasticity of the LC phase. Broadly, our study is helpful in understanding how form and function of cell membranes can be influenced by their local environment, which in-turn influences the distribution and reorganization of their heterogeneous constituents result in such widely varying material properties.

Example 8

Figure 12:
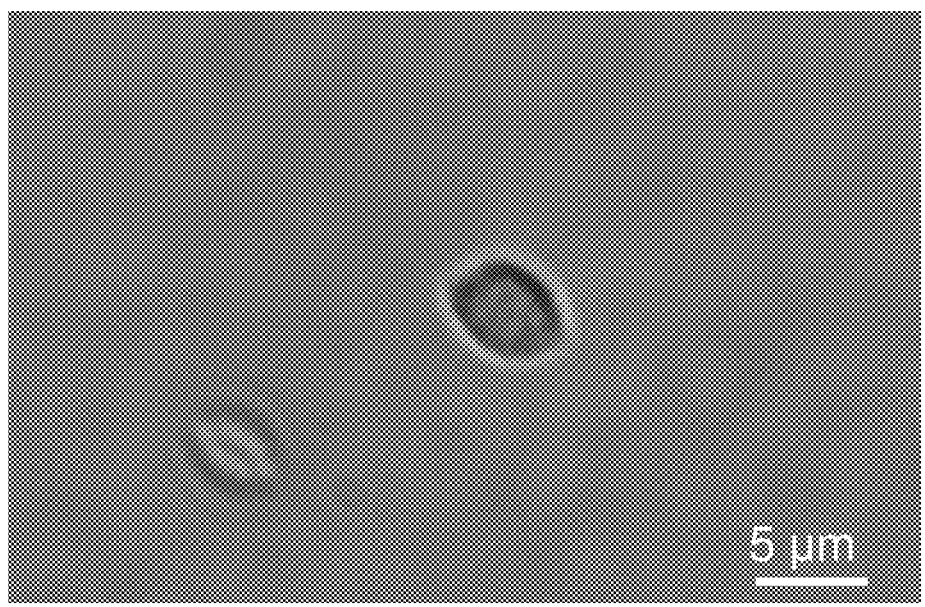
FIG. 12. Individual chloroplasts dispersed in 15 wt % DSCG.
Figure 13:
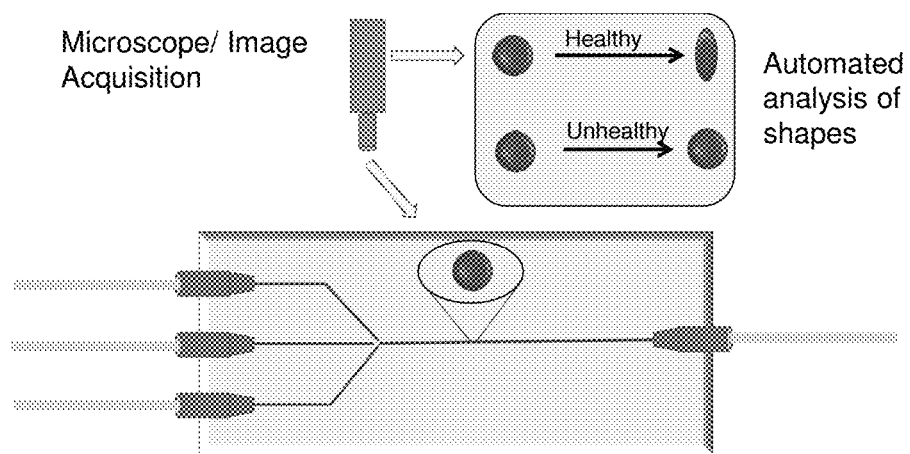
FIG. 13. An exemplary automated system for determining biomechanical properties and health status of cells.
Figure 14:
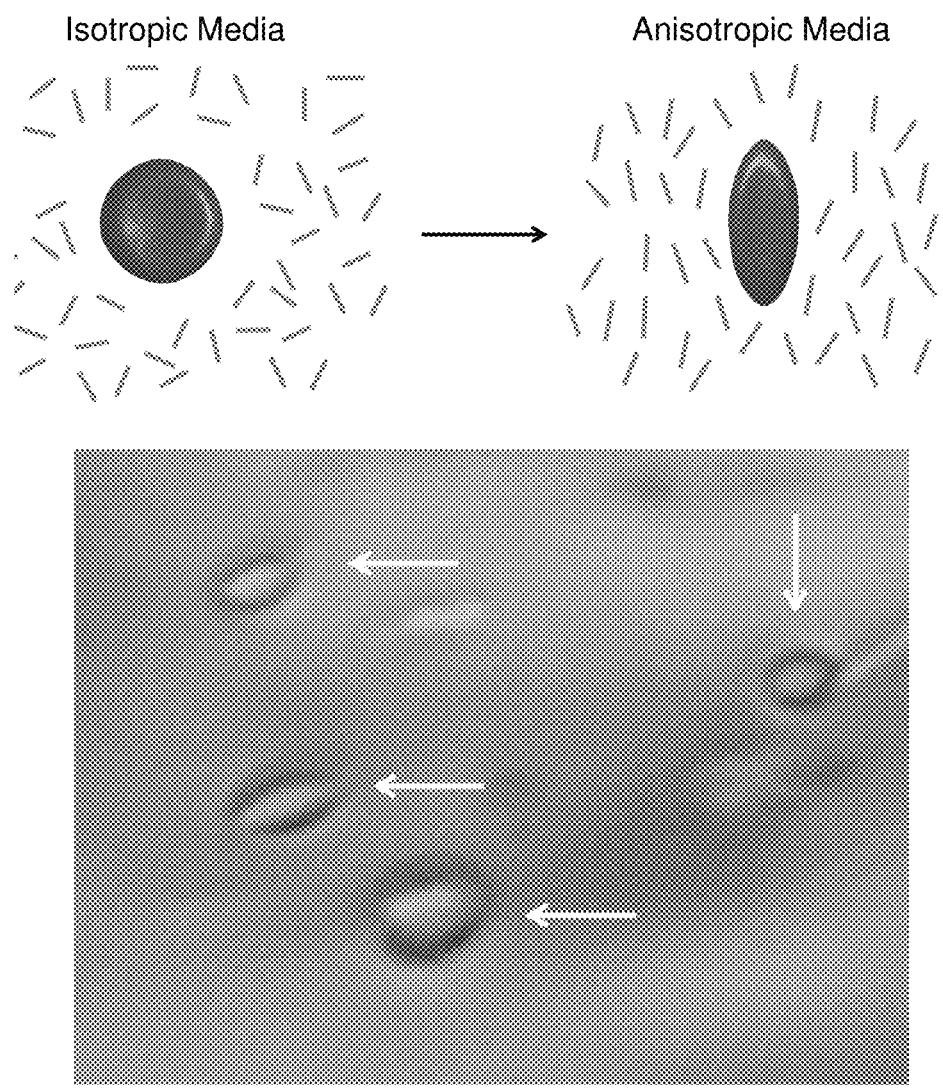
FIG. 14. An exemplary embodiment where part of the visual field is in isotropic state and another part of the visual field is in anisotropic state. Arrows show different cells in the visual field, some of which have been deformed due to increased elastic stress in the anisotropic state.

The inventors also show shape transformations of plant based organelles, namely chloroplasts, dispersed in DSCG. Briefly, chloroplasts that were extracted from spinach leaves and initially suspended in a sucrose buffer were transferred into a 20 wt % DSCG solution at a volume fraction of 1%. The sucrose buffer also contained percoll particles which were centrifuged and rinsed away before adding the buffer to the DSCG solutions. Upon dispersion in DSCG, we observed strained shapes of chloroplasts as presented in FIG. 12 with a two-dimensional aspect ratio~1.8. The anisometric shapes of the chloroplasts dispersed in DSCG indicate that the orientational elasticity of the LC is sufficiently large to strain the chloroplast membrane.

The data in this disclosure form the basis for simple diagnostic tools that can rapidly report the mechanical properties (and thus health) of mammalian or plant cells or organelles via dispersing the cells/organelles in LCs. Through careful and rigorous examination of shapes and asphericities adopted by RBCs in an LC host, it is possible to detect, through a single experiment, between a whole series of ailments for which the cell stiffness is the key variable.

What is claimed is:

1. A system, comprising:
   a liquid crystal material, wherein the liquid crystal material has a first state at a first condition and optionally a second state at a second condition;
   a device for holding a cell or an organelle of a cell, and the liquid crystal material, wherein the device is designed for use in optical imaging the cell or the organelle in the presence of the liquid crystal material at an isotonic concentration; and
   wherein the system is configured to compare a first state of the cell or the organelle in the first state of the liquid crystal material to a second state of the cell or the organelle at the second state of the liquid crystal material or a second state in an aqueous buffer to determine a biomechanical property of the cell or the organelle.

2. A composition, comprising a liquid crystal material at an isotonic concentration and a cell or an organelle of a cell,
   wherein the liquid crystal material has a first state at a first temperature or a first concentration and a second state at a second temperature or a second concentration, and
   wherein the cell or the organelle has a first state of the cell or the organelle in the first state of the liquid crystal material and a second state of the cell or the organelle at the second state of the liquid crystal material,
   such that the composition having the first state and the second state of the cell or the organelle in the liquid crystal material are configured to determine a biomechanical property of the cell or the organelle.

3. A method of evaluating a cell or an organelle of a cell, comprising:
   detecting a first state of the cell or the organelle in an aqueous buffer;
   detecting a second state of the cell or the organelle in a liquid crystal material;
   comparing the first state of the cell or the organelle to the second state of the cell or the organelle, thereby determining a biomechanical property of the cell.

4. A method of evaluating a cell or an organelle of a cell, comprising
   placing the cell or the organelle in a liquid crystal material at a first state, and detecting a first state of the cell or the organelle;
   effecting a change in the liquid crystal material from the first state to a second state, and detecting a second state of the cell or the organelle after the change;
   wherein the first state of the liquid crystal material is less ordered than the second state of the liquid crystal material, or the first state of the liquid crystal material is more ordered than the second state of the liquid crystal material; and
   comparing the first state of the cell or the organelle to the second state of cell or the organelle, thereby determining a biomechanical property of the cell or the organelle.

5. A method of evaluating cells or organelles, comprising:
   placing the cells or the organelles in a liquid medium, wherein a part of the liquid medium is in a liquid crystal state, and another part of the liquid medium is in an isotropic state, and wherein a first group of cells or organelles are in the part of the liquid medium that is in the liquid crystal state, and a second group of cells or organelles are in the part of the liquid medium that is in the isotropic state;
   detecting a state of the first group of cells or organelles and a state of the second group of cells or organelles; and
   comparing the state of the first group of cells or organelles to the state of the second group of cells or organelles, thereby determining a biomechanical property of the cells or the organelles.

6. The method of claim 5, wherein the state of the first group of cells or the organelles and the state of the second group of cells or the organelles comprise the shape of the cells or the organelles.

7. The method of claim 5, wherein a difference between the state of the first group of cells or organelles and the state of the second group of cells or organelles indicates the health status of the cells or the organelles.

8. The method of claim 3 or claim 4, wherein the liquid crystal material is at an isotonic concentration.

9. The method of claim 3 or claim 4, wherein the liquid crystal material is a lyotropic liquid crystal.

10. The method of claim 3 or claim 4, wherein the liquid crystal material is a lyotropic chromonic liquid crystal.

11. The method of claim 10, wherein the lyotropic liquid crystal is a non-amphiphilic liquid crystal.

12. The method of claim 11, wherein the non-amphiphilic liquid crystal is colloidal liquid crystal or liquid crystal comprised of polymers or oligomers.

13. The method of claim 3 or claim 4, wherein the cell is a eukaryotic cell.

14. The method of claim 13, wherein the cell is a mammalian cell or a plant cell.

15. The method of claim 14, wherein the mammalian cell is a human cell.

16. The method of claim 15, wherein the human cell is a red blood cell.

17. The method of claim 16, wherein the red blood cell is from a human suspected to be suffering from malaria or sickle cell anemia.

18. The method of claim 3, or claim 4, wherein the organelle is chloroplast.

19. The method of claim 3, claim 4, or claim 6, wherein the determining the shape of the cell comprises imaging the cell using an imaging apparatus.

20. The method of claim 19, wherein the imaging apparatus is selected from an optical microscope, a confocal microscope or a camera.

21. The system of claim 1, wherein the first condition comprises a first temperature, a first concentration, or both the first temperature and the first concentration, and optionally the second condition comprises a second temperature, a second concentration, or both the second temperature and the second concentration.

22. The system of claim 1, wherein the liquid crystal material is a lyotropic liquid crystal, the lyotropic liquid crystal is a non-amphiphilic liquid crystal, the non-amphiphilic liquid crystal is a colloidal liquid crystal.

23. The system of claim 1, wherein the liquid crystal material is a chromonic lyotropic liquid crystal.

24. The composition of claim 2, wherein the liquid crystal material is a lyotropic liquid crystal, the lyotropic liquid crystal is a non-amphiphilic liquid crystal, the non-amphiphilic liquid crystal is a colloidal liquid crystal.

25. The composition of claim 2, wherein the liquid crystal material is a chromonic lyotropic liquid crystal.

* * * * *